United States Patent
Matsushita

(10) Patent No.: US 9,615,854 B2
(45) Date of Patent: Apr. 11, 2017

(54) BEAUTY TOOL

(71) Applicant: MTG Co., Ltd., Nagoya-shi (JP)

(72) Inventor: Tsuyoshi Matsushita, Aichi (JP)

(73) Assignee: MTG Co., Ltd., Nagoya-shi (JP)

( * ) Notice: Subject to any disclaimer, the term of this patent is extended or adjusted under 35 U.S.C. 154(b) by 0 days.

(21) Appl. No.: 14/404,069

(22) PCT Filed: Jul. 11, 2013

(86) PCT No.: PCT/JP2013/068973
§ 371 (c)(1),
(2) Date: Nov. 26, 2014

(87) PCT Pub. No.: WO2014/024629
PCT Pub. Date: Feb. 13, 2014

(65) Prior Publication Data
US 2015/0150599 A1    Jun. 4, 2015

(30) Foreign Application Priority Data

Aug. 10, 2012 (JP) .................................. 2012-178653
Jun. 27, 2013 (JP) .................................. 2013-134480

(51) Int. Cl.
*A61N 1/32* (2006.01)
*A61B 17/52* (2006.01)
(Continued)

(52) U.S. Cl.
CPC .............. *A61B 17/52* (2013.01); *A61N 1/325* (2013.01); *A61N 2/06* (2013.01); *A45D 40/28* (2013.01);
(Continued)

(58) Field of Classification Search
CPC ...... A45D 2200/1063; A45D 2200/202; A45D 2200/207; A61B 17/52; A61N 1/325; A61N 1/328; A61N 1/08; A61H 15/02
(Continued)

(56) References Cited

U.S. PATENT DOCUMENTS 6,119,038 A * 9/2000 Cook ..................... A61N 1/044
604/20
6,694,183 B1 * 2/2004 Lehtoluoto ............ A61N 1/044
604/20
(Continued)

FOREIGN PATENT DOCUMENTS

| CN | 1333697 A | 1/2002 |
|---|---|---|
| CN | 203692812 U | 7/2014 |

(Continued)

OTHER PUBLICATIONS

International Search Report issued Aug. 27, 2013 in PCT/JP2013/068973 filed Jul. 11, 2013.
(Continued)

*Primary Examiner* — Laura Bouchelle
(74) *Attorney, Agent, or Firm* — Oblon, McClelland, Maier & Neustadt, L.L.P.

(57) ABSTRACT

A beauty tool (1) includes: a substantially rod-shaped main body (10); an attraction head (2) provided in the main body (10); and a beauty effect imparting part for imparting a beauty effect to human skin in a state where it is in contact with or close to the human skin. The attraction head (2) is provided at one end of the main body (10) and includes a magnetic force generating surface (20) for attracting and removing, by means of a magnetic force, a cosmetic agent applied to the human skin.

14 Claims, 15 Drawing Sheets

(51) Int. Cl.
*A61N 2/06* (2006.01)
*A45D 40/28* (2006.01)

(52) U.S. Cl.
CPC ............... *A45D 2200/1063* (2013.01); *A45D 2200/202* (2013.01); *A45D 2200/207* (2013.01)

(58) Field of Classification Search
USPC ............................................................ 607/3
See application file for complete search history.

(56) References Cited

U.S. PATENT DOCUMENTS

| | | | |
|---|---|---|---|
| 2002/0082668 | A1 | 6/2002 | Ingman |
| 2002/0193831 | A1* | 12/2002 | Smith, III ................ A61N 1/32 607/2 |
| 2005/0131497 | A1 | 6/2005 | Suzuki |
| 2009/0110704 | A1 | 4/2009 | Redaelli |
| 2015/0150599 | A1 | 6/2015 | Matsushita |

FOREIGN PATENT DOCUMENTS

| | | | |
|---|---|---|---|
| JP | 51-125982 A | 11/1976 | |
| JP | 2003-199620 A | 7/2003 | |
| JP | 2004-187874 A | 7/2004 | |
| JP | 2004-202022 A | 7/2004 | |
| JP | 2004-255018 A | 9/2004 | |
| JP | 2005-237545 A | 9/2005 | |
| JP | 2005-312497 A | 11/2005 | |
| WO | WO 2006/131997 A1 | 12/2006 | |
| WO | WO 2006131997 A1 * | 12/2006 | ......... A61H 23/0245 |

OTHER PUBLICATIONS

Chinese Office Action issued Apr. 20, 2016 in Patent Application No. 201310347714.5 (with English language translation).
Extended European Search Report issued Jan. 20, 2016 in Patent Application No. 13827435.2.
Office Action issued Mar. 15, 2016 in Japanese Patent Application No. 2013-134480 (with English language translation).
Combined Office Action and Search Report issued Jul. 31, 2015 in Chinese Patent Application No. 201310347714.5 (with English language translation and English translation of Category of Cited Documents).
Combined Office Action and Search Report issued Dec. 17, 2014 in Taiwanese Patent Application No. 102128470 (with English language translation and English translation of Category of Cited Documents).

* cited by examiner

BEAUTY TOOL

TECHNICAL FIELD

The present invention relates to a beauty tool used for beautifying human skin.

BACKGROUND ART

As a paste-like cosmetic agent used for beautifying skin, a cosmetic agent has been known which is applied to skin and removed after a while, whereby impurities, waste, and the like in the skin are removed together with the cosmetic agent. Such a cosmetic agent is roughly classified into: a cosmetic agent which turns into a film-like state with time after application thereof, and a cosmetic agent which maintains the paste form over time.

The cosmetic agent which turns into a film-like state after the application can be easily removed from the skin by holding a portion thereof and peeling off the film. On the other hand, as a method of removing the cosmetic agent which maintains the paste form even after the application from the skin, it is general to wipe off the cosmetic agent with cotton or the like, or rinse off the cosmetic agent with warm water or the like. Recently, a method of removing the used cosmetic agent more easily than these general methods has been desired.

For example, as disclosed in Patent Document 1 or Patent Document 2, there is proposed a method of using a skin cream blended iron powder and a remover including a magnet in its body in combination. By using the skin cream and the remover, the skin cream applied and used on the skin can be removed more easily than the conventional methods, and impurities and waste in the skin can be removed together with the iron powder contained in the skin cream.

Besides the process of removing impurities and waste from the skin, a process of imparting a beauty effect different from the removal of impurities and the like is also effective to enhance the beauty of the skin. As an example of such a process, there is a process of applying a skin lotion containing a beautifying component to skin, and allowing the beautifying component to infiltrate into the skin. When the beautifying component is infiltrated into the skin, a method such that the beautifying component is applied to the surface of the skin and naturally infiltrates into the skin over time is usually employed. Meanwhile, in recent years, as a method of promoting infiltration of beautifying components into skin, a method such that electrical treatment is performed using an ion introducer after a skin lotion containing an ionized component is applied to skin, as disclosed in Patent Document 3, for example.

PRIOR ART DOCUMENT

Patent Documents

Patent Document 1: JP-A-2005-312497
Patent Document 2: JP-A-2004-187874
Patent Document 3: JP-A-2005-237545

SUMMARY OF THE INVENTION

Problems to be Solved by the Invention

The process of removing impurities and waste from the skin and another process of imparting a beauty effect are, if performed in succession, more effective for enhancing the beauty of the skin. However, the cosmetic agent and the skin lotion used for these two processes and the remover and the ion introducer as supplemental tools for these processes have been individually developed, and have been concerned with only their respective processes. Therefore, when the two processes are actually performed in succession, the two different processes are separately performed, thereby causing the user feel to annoyed to no small extent.

The present invention has been made in view of the above background, and an object of the invention is to provide a beauty tool which contributes to improvement of convenience in successively performing the process of removing impurities and waste from the skin, and another process of imparting a beauty effect.

Solution to the Problems

One aspect of the present invention resides in a beauty tool, including:
a substantially rod-shaped main body;
an attraction head provided at one end of the main body, and having a magnetic force generating surface for attracting and removing, by means of a magnetic force, a cosmetic agent applied to human skin; and
a beauty effect imparting part provided at the other end of the main body, for imparting a beauty effect to the human skin in a state where the beauty effect imparting part is in contact with or close to the human skin.

Advantageous Effects of the Invention

The above-described beauty tool includes the attraction head for attracting and removing the cosmetic agent by the magnetic force at one end of the main body. Therefore, when a user holds the main body and brings the attraction head close to the skin surface on which the cosmetic agent is applied, the cosmetic agent is attracted to the attraction head due to the magnetic force. As a result, the beauty tool can easily remove the used cosmetic agent.

The beauty tool includes, at the other end of the main body, the beauty effect imparting part for imparting the beauty effect to the human skin while being in contact with or close to the human skin. Therefore, when the user holds the main body in a direction opposite to a direction when using the attraction head and activates the beauty effect imparting part in a state where the beauty effect imparting part is in contact with or close to the human skin, it is possible to impart the beauty effect to the human skin.

As described above, the beauty tool includes both the attraction head and the beauty effect imparting part. Therefore, the beauty tool can easily perform the process of removing impurities and waste from the skin with the cosmetic agent and another process of imparting the beauty effect, in succession, by using one tool. As a result, the user need not prepare and use different tools for the two processes.

As described above, according to the above aspect, it is possible to improve the convenience in successively performing the process of removing impurities and waste from the skin and another process of imparting a beauty effect.

DESCRIPTION OF THE PREFERRED EMBODIMENTS

Figure 1:
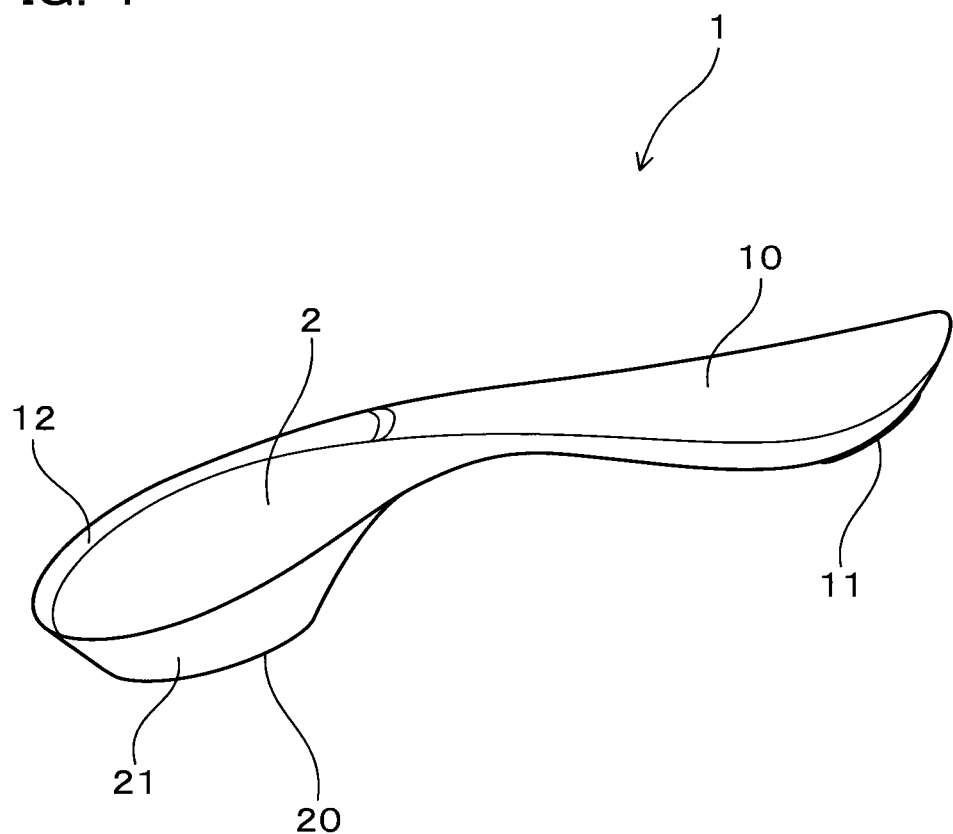
FIG. 1 is a perspective view of a beauty tool according to Example 1.

In the above-described beauty tool, the main body may have a shape which allows a user to hold the main body by hand, exposing an end portion thereof including a function to be used by the user. The specific shapes of the main body may have various configurations. The simplest configuration of the shape thereof is a columnar shape such as a cylindrical shape or a prismatic shape. Alternatively, as other configurations, the main body may have: a shape in which the outer diameter of the columnar shape is increased or decreased along the longitudinal direction of the main body; a shape bent in a direction perpendicular to the longitudinal direction; or a combination of these shapes.

Thus, the "substantially rod shape" indicating the shape of the main body is a concept including the geometrically-defined columnar shape, and a shape obtained by transforming the columnar shape to an extent that the transformed shape is recognized as a rod shape based on common sense.

A permanent magnet is preferably provided in the attraction head. In this case, it is easy to generate a relatively strong magnetic force from the attraction head stably. As a result, the beauty tool makes it easy to remove the used cosmetic agent from the skin, and thus the convenience for the user is further improved. In addition, when the permanent magnet is adopted, power for generating a magnetic force is dispensed with. As the permanent magnet, known permanent magnets such as ferrite magnet, neodymium magnet, samarium-cobalt magnet, and the like can be adopted.

On the other hand, an electromagnet may be provided in the attraction head. In this case, the beauty tool can switch between a state where a magnetic force is generated from the attraction head and a state where no magnetic force is generated from the attraction head. As a result, a magnetic force can be generated from the magnetic force generating surface only when attraction and removal of the cosmetic agent applied to the skin are performed. Therefore, the magnetic force from the magnetic force generating surface can be prevented from unintentionally acting on the surroundings of the beauty tool. Further, after the attraction and removal of the cosmetic agent from the skin, the cosmetic agent attracted onto the magnetic force generating surface can be easily removed from the beauty tool and discarded by switching the beauty tool to the state where no magnetic power is generated. Thus, the beauty tool having the electromagnet in the attraction head becomes more convenient.

The magnet used in the beauty tool is preferably a magnet that allows a magnetic force generated from the magnetic force generating surface to reach a more distant position, and more preferably, a magnet having magnetic characteristics that a magnetic flux density at a point 1 cm apart from the magnetic force generating surface is 36 mT or more. In this case, when the cosmetic agent is removed from the skin surface, the attraction head can attract the cosmetic agent even if the attraction head is apart from the skin. As a result, the beauty tool can efficiently remove the cosmetic agent from the skin surface.

The attraction head may have the magnetic force generating surface facing in a direction substantially perpendicular to the longitudinal direction of the main body. In this case, when the user holds the main body, the user can easily turn the magnetic force generating surface to the skin surface on which the cosmetic agent is applied. As a result, the beauty tool becomes more convenient for the user.

The beauty effect imparting part may have various configurations. For example, the beauty effect imparting part may be configured as: an ion introduction part that promotes infiltration of the charged beautifying component into the skin by means of a potential difference; an ion lead-out part that causes charged impurities, waste, and the like existing in the skin to migrate to the skin surface by means of a potential difference, and removes them; an ultrasonic wave generation part that gives ultrasonic wave vibration to the skin; a light irradiation part that irradiates the skin with a visible ray, a far infrared ray, and the like; an EMS (Electro Muscle Stimulation) part that gives weak electrical stimulation to the skin; and the like.

Among these, the beauty effect imparting part is preferably configured to include a working electrode for, when being in contact with the human skin, causing an ion introduction current to flow to the contact part, and a power supply for supplying power to the working electrode and a controller for controlling the current flowing to the contact part are provided in the main body. That is, the beauty tool is preferably configured to function as an ion introducer that promotes infiltration of the charged beautifying component into the skin by means of a potential difference. In this case, the beauty tool can easily reduce a preparation time required to start the process of promoting infiltration of the beautifying component after completion of the process of removing impurities and the like. Thereby, the beauty tool is expected to further enhance the effect of promoting infiltration of the beautifying component. Further, the beauty tool can further enhance the beauty effect that the user can feel.

The main body preferably includes, on a side opposed to the magnetic force generating surface, a counter electrode configured to be able to form a closed current path passing through the power supply and the human body together with the working electrode, and the working electrode is preferably disposed so as to face the side the magnetic force generating surface faces. That is, the counter electrode is preferably disposed on the opposite side from the magnetic force generating surface in the direction substantially perpendicular to the longitudinal direction of the main body. In this case, the beauty tool can reduce the possibility that the working electrode and the counter electrode are simultaneously in contact with the surface where the beauty tool is placed when the beauty tool is placed on a desk or the like. Therefore, the beauty tool can reduce the possibility that the working electrode and the counter electrode are conducted with each other via the surface where the beauty tool is placed, and thus the power consumption is easily reduced. As a result, the convenience for the user is further improved. In addition, when both the working electrode and the counter electrode are in contact with the human body, a closed current path is formed passing through the power supply and the human body. As a result, the ion introduction current can be caused to flow to the human body more efficiently, and thus the beauty effect can be further enhanced.

The controller may be configured to include: means to apply a pulse voltage to the working electrode, and measure an electrical characteristic value in the controller by using the pulse voltage; means to determine whether or not the working electrode is in contact with the human body, based on the electrical characteristic value; and means to cause the ion introduction current to flow to the contact part when it is determined that the working electrode is in contact with the human body. The controller may be configured to, when it is determined that the working electrode is not in contact with the human body, perform the measurement of the electrical characteristic value and the determination again after waiting for a lapse of a predetermined time by using a delay timer.

In this case, the beauty tool can cause the ion introduction current to flow to the contact part in response to the working electrode coming in contact with the human body, without the necessity of an additional switching operation. Thereby, the user can easily obtain the effect of promoting infiltration of the beautifying component by only bringing the working electrode into contact with a portion where the user desires the beauty effect. Therefore, the beauty tool becomes more convenient.

Further, the beauty tool is configured to perform the measurement of the electrical characteristic value and the determination again after waiting for a lapse of a predetermined time by using the delay timer in case that it is determined that the working electrode is not in contact with the human body. Thereby, the frequency of performing the measurement of the electrical characteristic value and the determination can be reduced. In addition, power consumption regarding the pulse voltage used for the measurement of the electrical characteristic value can be minimized. As a result, the beauty tool can reduce the power consumption in the standby state, namely, the state where the working electrode is not in contact with the human body.

The controller may be configured to include a reflux section which takes in the current flowing through the human body and refluxes the current to the power supply, measure, as the electrical characteristic value, a difference of a potential in the reflux section with respect to a ground potential, and determine that the working electrode is in contact with the human body when the potential difference is equal to or larger than a predetermined threshold.

For example, a current value, a voltage value, a resistance value, and the like can be used as the electrical characteristic value. Among these, a potential difference (a voltage value) is preferred as the electrical characteristic value in terms of simplification of the circuit configuration.

The circuit configuration of the controller varies depending on whether the working electrode is in contact with the human body or not. Therefore, a part measuring the electrical characteristic value is preferred to be a part where a response to the pulse voltage varies relatively largely depending on the contact state of the working electrode. In particular, the reflux section is preferred as the part where the electrical characteristic value is measured because a potential difference occurs in response to the pulse voltage when the working electrode is in contact with the human body while no potential difference occurs when the working electrode is not in contact with the human body. As a result, the beauty tool can increase the accuracy of the determination as to whether the working electrode is in contact with the human body or not.

The waveform of the ion introduction current flowing to the contact part with the skin is controlled by the controller. As the waveform of the ion introduction current, various waveforms can be adopted such as a DC current having constant current and voltage, a pulse current, a sine wave AC current, and the like, and some of these waveforms may be combined.

Among these, the ion introduction current preferably has a waveform that allows the following steps to be successively repeated: an ion introduction step of causing a current of one polarity to flow to the contact part; a reset pulse step of causing a pulse current of the other polarity to flow to the contact part; and a skin care step of causing a current whose polarities alternately change to flow to the contact part.

In the ion introduction step, the current of one polarity flows from the working electrode to the contact part. The polarity of the current is controlled to be the same as the polarity of the electric charge of the beautifying component. It is noted that the polarity of the current is positive in the direction from the working electrode to the skin, and negative in the opposite direction. For example, when the beautifying component has a negative charge, a voltage is applied to each electrode such that the potential of the working electrode is negative with respect to the ground potential. Thereby, the current is controlled so as to have the negative polarity. Then, the beautifying component having the negative charge is subjected to repulsion from the working electrode and becomes more likely to promote to infiltrate into the skin.

In the skin care step, a weak current whose polarities alternately change flows between the both electrodes. When the weak current flows through the skin, skin cells are activated, and thus it is possible to achieve advantageous effects such as smooth flow of lymph, promoted circulation of blood, enhanced metabolism, and the like. Therefore, beauty effects such as recovery of skin firmness, beautification of skin, and the like can be expected by performing the skin care step.

By supplying the ion introduction current that allows the ion introduction step, the reset pulse step, and the skin care step to be repeated in this order to the skin surface where the beauty effect is desired, the beauty tool is expected to further enhance the beauty effect by synergy of the effect of promoting infiltration of the beautifying component and the effect of activating the skin.

The beauty tool may be provided with an attachable/detachable cover member that covers the magnetic force generating surface on the attraction head. In this case, the used cosmetic agent is attracted toward the magnetic force generating surface due to the magnetic force, and adhered to the surface of the cover member. Therefore, the beauty tool can prevent direct adherence of the cosmetic agent onto the magnetic force generating surface. Further, discard of the used cosmetic agent can be easily performed by detaching the cover member from the magnetic force generating surface together with the cosmetic agent.

The shape, the material and the like of the cover member can employ various configurations without being limited, as long as the cover member can cover the magnetic force generating surface. The simplest example of the cover member is a sheet or pouch-like cover member which is placed so as to cover the magnetic force generating surface and is held by the user together with the beauty tool.

The cover member may comprise a cover body that covers the magnetic force generating surface, and a retaining means that retains the cover body on the magnetic force generating surface, and the retaining means may be formed of a magnet sheet. In this case, after the cover member is detached from the magnetic force generating surface, the used cosmetic agent is retained on the surface of the cover member due to the magnetic force generated from the magnet sheet. As a result, the used cosmetic agent is prevented from unintentionally falling from the cover member and spattering. The magnet sheet is a known magnet sheet obtained by dispersing powdery permanent magnet in a resin, and forming the resin into a sheet shape.

The cover body may be configured to have a double-layer structure obtained by putting two layers together and joining the peripheral edges thereof so that an insertion opening is formed, and allow the magnet sheet to be inserted from the insertion opening and placed in a housing space formed between the two layers. In this case, the magnet sheet is attachable to and detachable from the cover body, and thus only the cover body can be replaced. Therefore, the cover body to which the used cosmetic agent is attracted can be replaced with a new cover body, and the cosmetic agent can be discarded together with the cover body. As a result, disposal of the used cosmetic agent is facilitated. In addition, the cover body can be easily kept clean.

The cover body and the magnet sheet may be joined with each other. In this case, after the cover member is removed from a swelling portion, the used cosmetic agent is retained on the surface of the cover member due to magnetic force generated from the magnet sheet. As a result, the used cosmetic agent is prevented from unintentionally falling from the cover member and spattering. In this case, the cover body and the magnet sheet can be joined by various methods such as adhesive and hook and loop fastener.

The cover body may be formed of a cotton sheet. In this case, when the cotton sheet comes in contact with the skin, stimulus to the skin is easily reduced. Thus, the user can conform the beautifying component to the skin or remove the excessive beautifying component by using the cotton sheet contacting the skin. As a result, the beauty effect can be further enhanced.

The cover member may be detachably attached to the swelling portion of the attraction head of the beauty tool, which swelling portion is formed by causing the magnetic force generating surface to swell from the body, and the cover member may comprise a bottom surface portion facing the magnetic force generating surface and a substantially cup-like shape similar to the shape of the swelling portion and may be configured to be inside-outside reversely transformable such that the projecting direction of the bottom surface portion is reversible.

The cover member, when it is used, is attached to the swelling portion while having the substantially cup-like shape swelled the bottom surface portion side facing the magnetic force generating surface, as described above. Therefore, when the swelling portion of the beauty tool to which the cover member is attached is brought close to the skin surface on which the cosmetic agent is applied, the cosmetic agent is attracted to a convex surface of the cover member, i.e., the surface of the bottom surface portion and its vicinity, due to the magnetic force. There are various methods of discarding the used cosmetic agent attracted on the surface of the cover member. For example, the following method may be adopted.

After the cosmetic agent is removed from the skin surface, the bottom surface portion of the cover member is held between the attracted cosmetic agent and the swelling portion by the magnetic force, and is maintained to be in contact with the magnetic force generating surface of the swelling portion. In this state, the user of the beauty tool, with the surface (on which the cosmetic agent is placed) of the bottom surface portion of the cover member facing upward, transforms the cover member by pulling off a portion of the cover member surrounding the bottom surface portion from the surface of the swelling portion in the upward direction.

In the state where transformation of the portion surrounding the bottom surface portion of the cover member is completed, the overall shape of the cover member is a substantially cup-like shape obtained by transforming the cover member to be reversed inside out such that the projecting direction of the bottom surface portion is reversed with respect to the initial attachment state. That is, the inside-outside reverse transformation causes the convex surface of the cover member to be a concave surface. Thereby, the used cosmetic agent having been attracted to the bottom surface portion of the cover member and its vicinity is collected in the cup-shaped cover member having an opening facing upward.

Then, the inside-outside reversely transformed cover member is pulled off from the swelling portion of the beauty tool, and thereby the effect of the magnetic force from the swelling portion on the cosmetic agent in the cover member can be eliminated. At this time, since the cover member is inside-outside reversely transformed, the used cosmetic agent is stored in the cover member. Therefore, when the cover member is pulled off from the swelling portion, unintentional spattering of the cosmetic agent can be prevented.

Thereafter, the used cosmetic agent can be easily removed from the surface of the cover member by bringing the cover member above a place where the cosmetic agent is to be discarded, and turning the surface with the cosmetic agent downward to urge natural falling of the cosmetic agent due to its own weight or performing a process of removing the cosmetic agent with paper or the like. The cover member from which the cosmetic agent has been removed is again transformed to be reversed inside out and attached to the swelling portion of the beauty tool, and thus the cover member can be used again.

As described above, the cover member can be detachably attached to the swelling portion, and has the substantially cup-like shape that is inside-outside reversely transformable. Thereby, as described above, the used cosmetic agent having been removed from the skin with the beauty tool is prevented from unintentionally spattering, and thus the convenience of the beauty tool can be further improved.

The cover member is preferably formed of a material having elasticity. As the material of the cover member, various materials can be used as long as they have flexibility that allows the cover member to be inside-outside reversely transformable. For example, rubber, resin, paper, nonwoven fabric, and the like can be used. Among these, in particular, the cover member formed of a material having elasticity can be easily transformed to be reversed inside out. Moreover, it is very easy to restore such cover member to its initial shape. Examples of the material having elasticity include rubber, resin, and the like, and more specifically, silicone rubber, urethane rubber, polyethylene, and the like.

The cover member may have the flat bottom surface portion, and a sidewall portion extending from the outer peripheral edge of the bottom surface portion so as to have a gradually increasing diameter. In this case, the cover member can be transformed to be reversed inside out by displacing only the sidewall portion with the position of the bottom surface portion being kept. Therefore, the process of reversing the cover member inside out is facilitated, and thus spattering of the cosmetic agent from the cover member can be prevented more reliably.

EXAMPLES

Example 1

Figure 2:
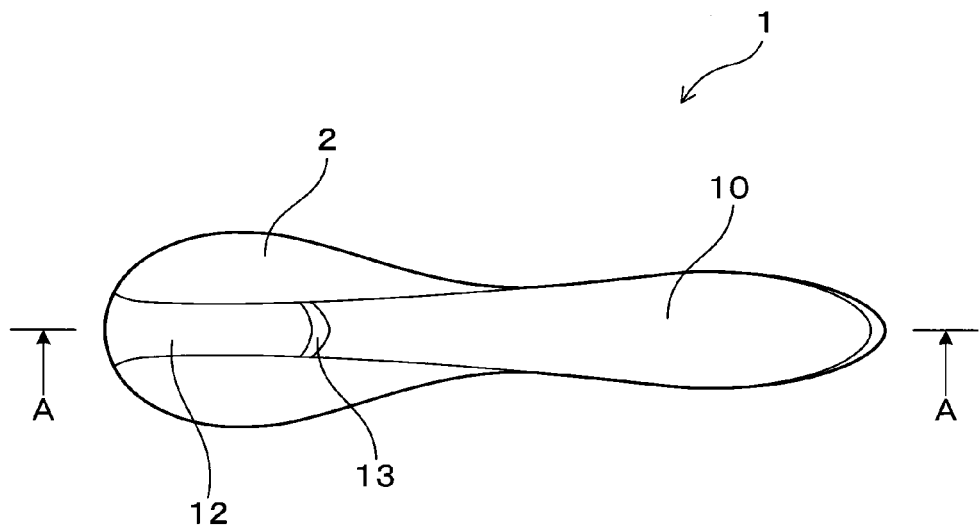
FIG. 2 is a plan view of the beauty tool according to Example 1, as viewed from the side (upper side) opposite to a magnetic force generating surface.
Figure 3:
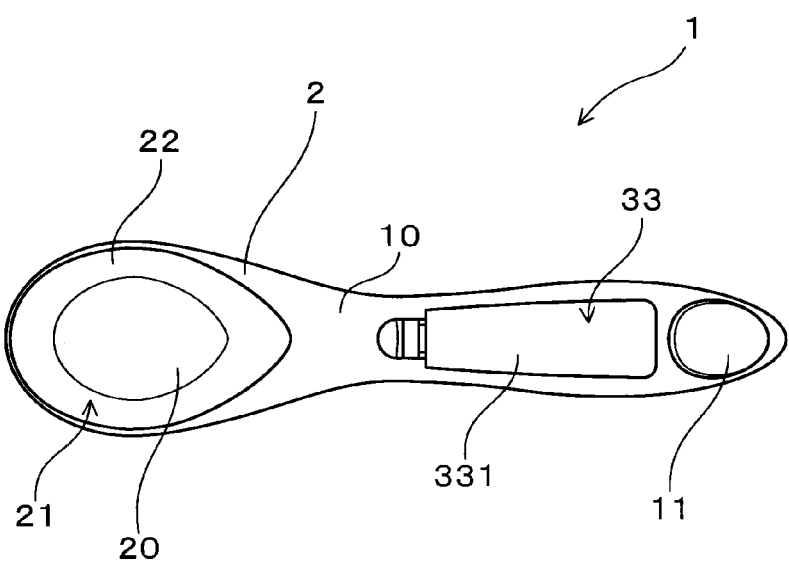
FIG. 3 is a plan view of the beauty tool according to Example 1, as viewed from the side (lower side) on which the magnetic force generating surface is present.
Figure 4:
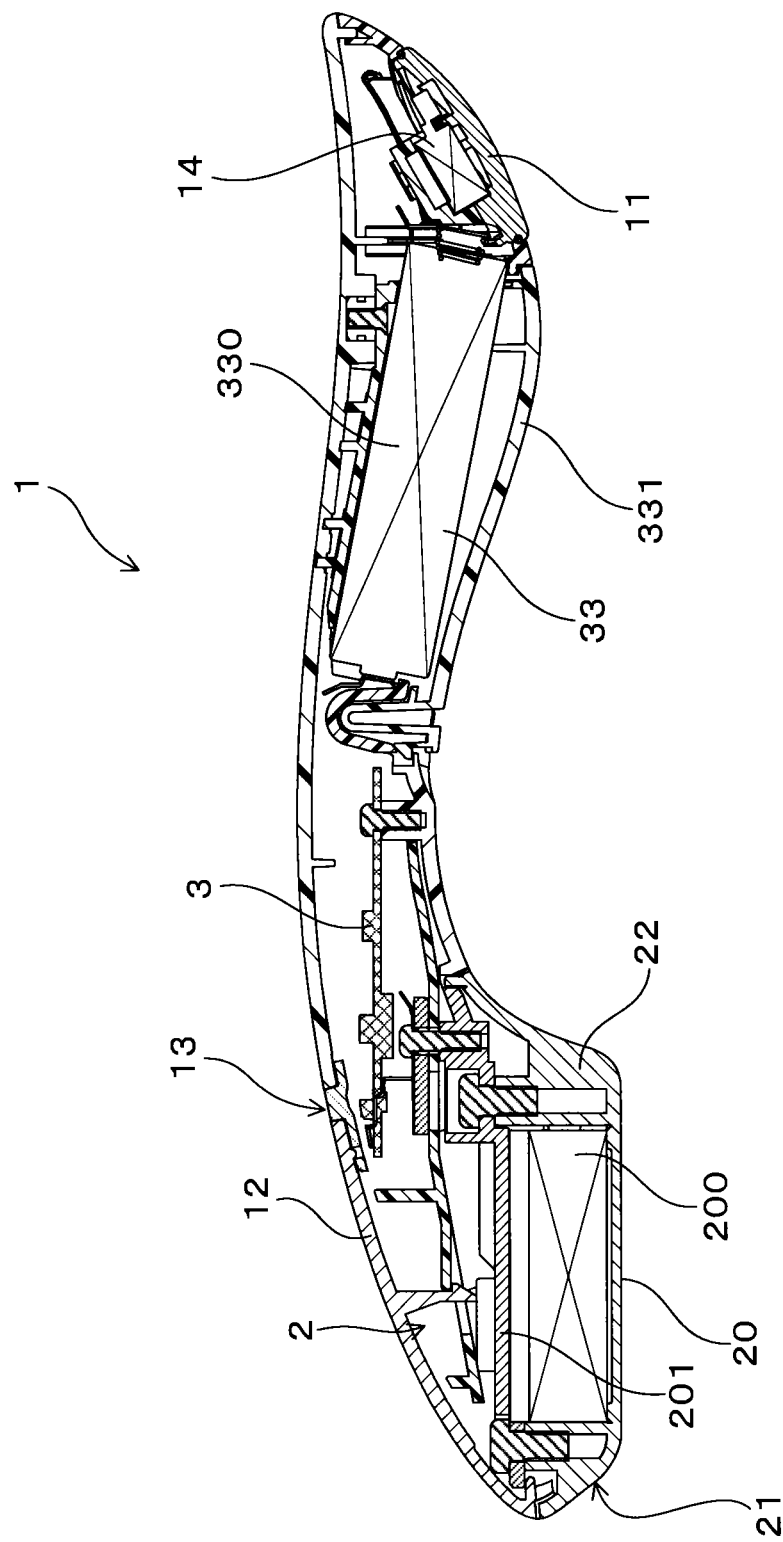
FIG. 4 is a cross-sectional view as viewed from the direction of arrows A-A in FIG. 2.

An example of the above-described beauty tool will be described with reference FIGS. 1 to 11. As shown in FIG. 1, a beauty tool 1 includes a substantially rod-shaped main body 10, an attraction head 2 provided at one end of the main body 10, and a beauty effect imparting part provided at the other end of the main body 10. As shown in FIG. 3 and FIG. 4, the attraction head 2 has a magnetic force generating surface 20 for attracting and removing a cosmetic agent 4 applied to human skin by means of a magnetic force. The beauty effect imparting part has a working electrode 11 shown in FIG. 11, and is configured to cause an ion introduction current to flow to the contact part while being in contact with the human skin. As shown in FIG. 4, a power supply 33 for supplying power to the working electrode 11 and a controller 3 for controlling the current flowing to the contact part are embedded in the main body 10.

Hereinafter, the beauty tool 1 will be described in detail. As shown in FIGS. 1 to 3, the main body 10 of the beauty tool 1 includes the attraction head 2 at one end, and a counter electrode 12 configured to be able to form a closed current path passing through the power supply 33 and a human body together with the working electrode 11. The main body 10 includes the working electrode 11 at the other end. A cover member (not shown) can be detachably attached to the magnetic force generating surface 20 of the attraction head 2, as described later. It is noted that, hereinafter, in the longitudinal direction of the main body 10, a side on which the working electrode 11 is provided may be referred to as a front side, and a side on which the attraction head 2 is provided may be referred to as a rear side. In addition, when the beauty tool 1 is viewed in the front-rear direction, a side on which the magnetic force generating surface 20 is provided may be referred to as a lower side, and a side opposite to the lower side may be referred to as an upper side. Further, a direction perpendicular to both the front-rear direction and the upper-lower direction may be referred to as a lateral direction. These directional expressions are merely for convenience, and are not related to the actual direction of the beauty tool 1 when being used.

As shown in FIG. 1 and FIG. 4, the main body 10 has a substantially arc shape as viewed in the lateral direction, and curves so that a substantially center portion thereof in the front-rear direction (longitudinal direction) is positioned higher than both end portions thereof. As shown in FIGS. 2 and 3, the both end portions of the main body 10 in the front-rear direction each have a substantially arc-shaped outline as viewed in the upper-lower direction. In addition, the center portion of the main body 10 in the longitudinal direction is formed to be narrower in width than the both end portions as viewed in the upper-lower direction.

As shown in FIG. 1, the attraction head 2 provided in the rear end portion of the main body 10 has a swelling portion 21 that swells toward the lower side from the main body 10. In addition, the swelling portion 21 has the magnetic force generating surface 20 at a top surface thereof.

As shown in FIG. 4, the swelling portion 21 has the magnetic force generating surface 20 which is a flat surface, and a head sidewall 22 extending from an outer peripheral edge of the magnetic force generating surface 20. As shown in FIG. 3, the magnetic force generating surface 20 has a substantially elliptical shape as viewed from the lower side, and is disposed with a longitudinal axis thereof along the front-rear direction (longitudinal direction). As shown in FIG. 4, the diameter of the head sidewall 22 is gradually increased upward from the outer peripheral edge of the magnetic force generating surface 20. The magnetic force generating surface 20 and the head sidewall 22 are connected to each other by a gentle curved surface.

As shown in FIG. 4, a substantially cylindrical permanent magnet 200 is provided in the swelling portion 21 of the attraction head 2. In the swelling portion 21, the permanent magnet 200 is disposed so that one end surface thereof is in contact with an internal wall surface of the magnetic force generating surface 20. An end surface, of an outer peripheral surface of the permanent magnet 200, opposite to the magnetic force generating surface 20 is covered with a yoke member 201 formed of a soft magnetic material. Thereby, the beauty tool 1 is configured so that a magnetic force generated from the permanent magnet 200 acts more strongly in the lower direction.

The permanent magnet 200 of the present example is a neodymium magnet which is polarized in its height direction. By using the neodymium magnet, a magnetic flux density at the surface of the magnetic force generating surface 20 has a maximum value of 286 mT. In addition, a magnetic flux density measured at a point 20 mm apart from the center portion of the magnetic force generating surface 20 in the lower direction is 43 mT.

As shown in FIG. 2, the main body 10 includes the counter electrode 12 disposed on the side (upper side) opposite to the magnetic force generating surface 20. As shown in FIG. 3, the working electrode 11 is disposed so as to face the side the magnetic force generating surface 20 faces (lower side). Each of the working electrode 11 and the counter electrode 12 is formed so that the width thereof in the lateral direction is narrower than the maximum width of the main body 10.

In the main body 10, as shown in FIG. 4, the power supply 33, the controller 3, an LED indicator 13, and a vibration motor 14 are provided. The power supply 33 is disposed between the center of the main body 10 in the longitudinal direction and the working electrode 11, and is configured so that a battery 330 can be housed in a space in the main body 10. As shown in FIGS. 3 and 4, the battery 330 is retained in the main body 10 when a lid 331, which is attachable to and detachable from the main body 10, is attached to the main body 10.

The controller 3 is disposed on the attraction head 2 side with respect to the center of the main body 10 in the longitudinal direction. As shown in FIGS. 2 and 4, the LED indicator 13 is disposed at a substantially center position in the main body 10 in the longitudinal direction. The LED indicator 13 is configured to emit light upward when an ion introduction current flows from the working electrode 11 to the skin. The vibration motor 14 is disposed at an end portion on the working electrode 11 side in the main body 10. The vibration motor 14 is configured to be driven and generate vibration when the ion introduction current flows from the working electrode 11 to the skin.

Hereinafter, electrical connections among the components of the beauty tool 1 will be described with reference to FIG. 5. The power supply 33 is connected to a control microcomputer 30 and a voltage applying section 31 in the controller 3, to the LED indicator 13, and to the vibration motor 14, and supplies power for operation to these components.

Further, the controller 3 is connected to each of the power supply 33, the working electrode 11, the counter electrode 12, the LED indicator 13, and the vibration motor 14, and is configured to be able to control the operations of these components. The controller 3 includes the control microcomputer 30, the voltage applying section 31, and a reflux section 32. The control microcomputer 30 has a function of inputting and outputting a signal for controlling the operations of the respective components. The voltage applying section 31 has a function of applying a voltage between the working electrode 11 and the counter electrode 12. The reflux section 32 has a function of taking in a current flowing through the human body, and refluxing the current to the power supply 33 from the working electrode 11 or the counter electrode 12.

The control microcomputer 30 and the voltage applying section 31 are connected to each other so that a voltage control signal and a current value selection signal, which are described later, can be transmitted therebetween. The reflux section 32 is disposed between the voltage applying section 31 and a grounding section 312 connected to a minus pole of the power supply 33. In addition, the reflux section 32 is connected to a later-described ADC (Analog to Digital Converter) 300 in the control microcomputer 30. Thereby, the controller 3 is configured to be able to input a potential difference in the reflux section 32 to the control microcomputer 30.

The control microcomputer 30 includes the ADC 300, a calculation section 301, a signal output section 302, and a delay timer 303. The ADC 300 has a function of digitalizing the potential difference in the reflux section 32. The calculation section 301 has a function of determining whether or not the working electrode 11 and the counter electrode 12 are in contact with the human body. The signal output section 302 has a function of controlling a current supplied from the working electrode 11 to the surface of skin on which a beauty effect is desired.

The ADC 300 is connected to the reflux section 32 of the controller 3, and is configured to digitalize the potential difference of the reflux section 32 with respect to the potential of the grounding section 312 (hereinafter, the potential of the grounding section 312 is referred to as "ground potential"). The value of the potential difference digitized by the ADC 300 is transferred to the calculation section 301 in the control microcomputer 30.

The calculation section 301 compares the value of the potential difference inputted from the ADC 300 with a predetermined threshold. The calculation section 301 is configured to determine that at least one of the working electrode 11 and the counter electrode 12 is not in contact with the human body when the value of the potential difference is smaller than the predetermined threshold, and determine that both the working electrode 11 and the counter electrode 12 are in contact with the human body when the value of the potential difference is equal to or larger than the predetermined threshold. Further, the calculation section 301 is configured to be able to control a signal outputted from the signal output section 302, based on both the result of the above determination and a predetermined operation flow shown in FIGS. 6 and 7. The operation flow will be described later in detail.

The signal output section 302 is configured to output the voltage control signal and the current value selection signal to the voltage applying section 31, upon receiving a control signal from the calculation section 301. The voltage control signal is input to a later-described polarity inversion circuit 310 in the voltage applying section 31, and controls on/off and the polarity of a voltage applied between the working electrode 11 and the counter electrode 12. The current value selection signal is input to a later-described constant current circuit 311 in the voltage applying section 31, and controls the value of a current flowing between the working electrode 11 and the counter electrode 12.

The signal output section 302 is also connected to the LED indicator 13 and to the vibration motor 14. The signal output section 302 is configured to output driving signals for driving the LED indicator 13 and the vibration motor 14, when the result of the determination by the calculation section 301 is that both the working electrode 11 and the counter electrode 12 are in contact with the human body.

The delay timer 303 is activated by the calculation section 301 when the result of the determination by the calculation section 301 is that at least one of the working electrode 11 and the counter electrode 12 is not in contact with the human body. The delay timer 303 has a function of suspending the operation of the calculation section 301 for a predetermined time. Thereby, in the beauty tool 1, the operation of each component is suspended in association with the suspension of the operation of the calculation section 301 during a period from when the delay timer 303 is activated to when the predetermined time elapses. In addition, the delay timer 303 is configured to resume the operation of the calculation section 301 after the predetermined time has elapsed.

The voltage applying section 31 includes the polarity inversion circuit 310 and the constant current circuit 311, and is configured so that these circuits are connected to each other. In addition, the polarity inversion circuit 310 and the signal output section 302 of the control microcomputer 30 are connected to each other. The polarity inversion circuit 310 is connected to the working electrode 11 and to the counter electrode 12. Thereby, the polarity inversion circuit 310 is configured to be able to control the potential difference between the working electrode 11 and the counter electrode 12, based on the voltage control signal outputted from the signal output section 302.

The constant current circuit 311 has a function of keeping the current flowing between the working electrode 11 and the counter electrode 12 at a constant value. The constant current circuit 311 and the signal output section 302 of the control microcomputer 30 are connected to each other. The constant current circuit 311 is configured to be able to set, in two levels, the current flowing between the working electrode 11 and the counter electrode 12, based on the current value selection signal outputted from the signal output section 302. In the present example, the magnitude of this current is set in two levels, i.e., an ion introduction level, and a skin care level at which the current value is smaller than that at the ion introduction level. The ion introduction level is applied during execution of an ion introduction step S8 and a reset pulse step S9, and the skin care level is applied during execution of a skin care step S11, which steps are described later.

The reflux section 32 includes a resistor 320 connected between the voltage applying section 31 and the grounding section 312. Thereby, the current taken in from the voltage applying section 31 side flows through the resistor 320 toward the grounding section 312, and is refluxed to the minus pole of the power supply 33 via the grounding section 312. In the reflux section 32, a point between the voltage applying section 31 and the resistor 320 is connected to the ADC 300 of the control microcomputer 30. Thereby, the ADC 300 is configured so that a potential difference at the point between the voltage applying section 31 and the resistor 320 with respect to the ground potential is input to the ADC 300.

Next, the operation flow of the beauty tool 1 will be described with reference to FIGS. 6 and 7. When power is supplied from the power supply 33 to the beauty tool 1, the beauty tool 1 performs step S1 to initialize the control microcomputer 30. At this time, the control microcomputer 30 outputs a current value selection signal to the constant current circuit 311 so as to set the current value to the ion introduction level.

Thereafter, the control microcomputer 30 performs step S2 to cause the delay timer 303 to wait for a lapse of the above-mentioned predetermined time. The delay timer 303 of the present example can appropriately set the predetermined time within a range of 50 to 1000 msec.

Subsequent to step S2, the control microcomputer 30 performs step S3 to cause the power supply 33 to supply power for operation to the voltage applying section 31, and causes the signal output section 302 to output a voltage control signal. Thereby, the control microcomputer 30 applies a pulse voltage once between the working electrode and the counter electrode 12 while controlling a potential difference between these electrodes so that the potential of the working electrode 11 is lower than that of the counter electrode 12. Thus, step S4 is performed in which the pulse voltage is applied once between the working electrode 11 and the counter electrode 12. In the present example, the value of the pulse voltage in step S4 is 5 V.

Figure 6:
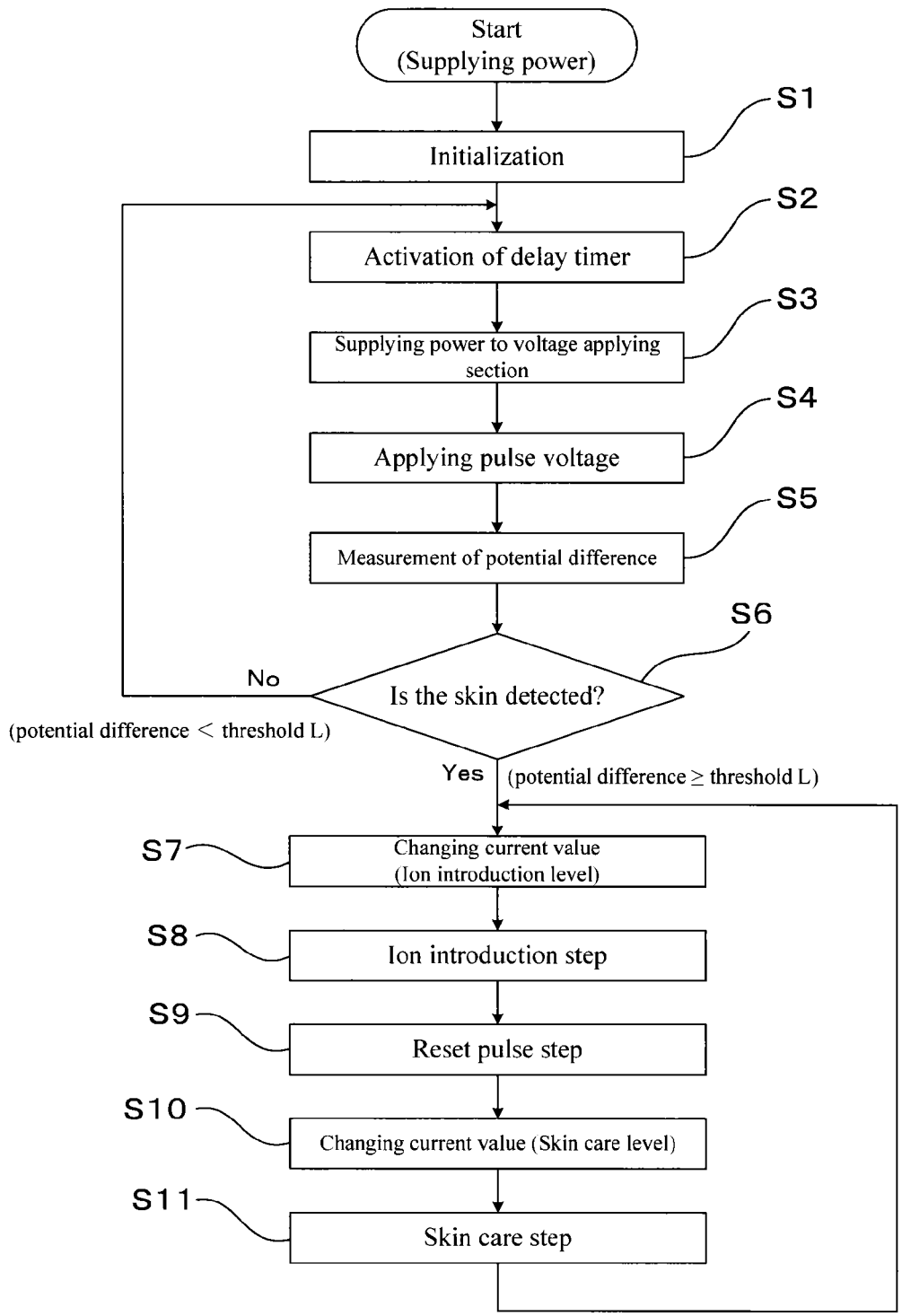
FIG. 6 is a flowchart illustrating the operation of the beauty tool according to Example 1.

Subsequently, as shown in FIG. 6, step S5 to measure a potential difference in the reflux section 32 is performed. In step S5, when both the working electrode 11 and the counter electrode 12 are in contact with the skin, a pulse current due to the above-described pulse voltage flows from the counter electrode 12 via the human body to the working electrode 11. This pulse current is taken from the working electrode 11 into the controller 3, and causes a potential difference between the both ends of the resistor 320 in the reflux section 32 as shown by a waveform F1 in FIG. 8. Then, the potential difference caused between the both ends of the resistor 320, namely, the potential difference in the reflux section 32 with respect to the ground potential, is input to the ADC 300 of the control microcomputer 30, wherein the value of the potential difference is measured.

On the other hand, when at least one of the working electrode 11 and the counter electrode 12 is not in contact with the skin, no current flows to the resistor 320 even if the pulse voltage is applied, and no potential difference occurs between the both ends of the resistor 320. Therefore, when at least one of the working electrode 11 and the counter electrode 12 is not in contact with the skin, the value of the potential difference is 0 V.

Figure 8:
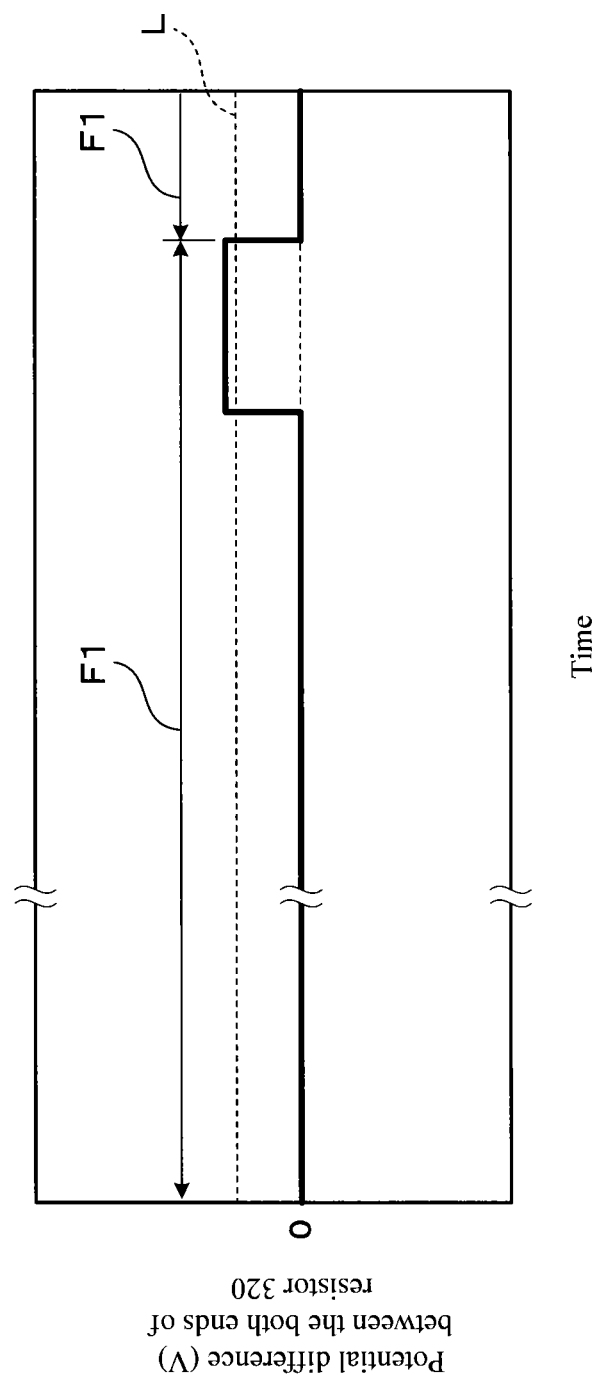
FIG. 8 is a diagram showing a waveform of a potential difference that occurs between both ends of a resistor in step S5, in a case where a working electrode and a counter electrode of the beauty tool of Example 1 are in contact with a human body.

Thereafter, the control microcomputer 30 performs step S6 to cause the calculation section 301 to determine the contact state of the working electrode 11 and the counter electrode 12 with the human body, based on a result of comparison between the potential difference and a predetermined threshold L (refer to FIG. 8). When the potential difference measured in step S5 is smaller than the threshold L, the control microcomputer 30 determines that at least one of the working electrode 11 and the counter electrode 12 is not in contact with the human body ("No" in step S6). In this case, the control microcomputer 30 returns to step S2 and activates the delay timer 303. While it is determined in step S6 that at least one of the working electrode 11 and the counter electrode 12 is not in contact with the human body, the control microcomputer 30 repeats steps S2 to S6. In the present example, the threshold L can be appropriately set within a range of 50 to 200 mV.

On the other hand, as shown in FIG. 8, when the potential difference in the reflux section 32 with respect to the ground potential is equal to or larger than the threshold L in step S6, the control microcomputer 30 determines that both the working electrode 11 and the counter electrode 12 are in contact with the human body ("Yes" in step S6). In this case, as shown in FIG. 6, the control microcomputer 30 performs step S7 to output a current value selection signal to the constant current circuit 311 so as to set the current value to the ion introduction level. Subsequent to step S7, the control microcomputer 30 transmits a voltage control signal to the voltage applying section 31 so that an ion introduction current flows from the working electrode 11 to the skin.

Figure 9:
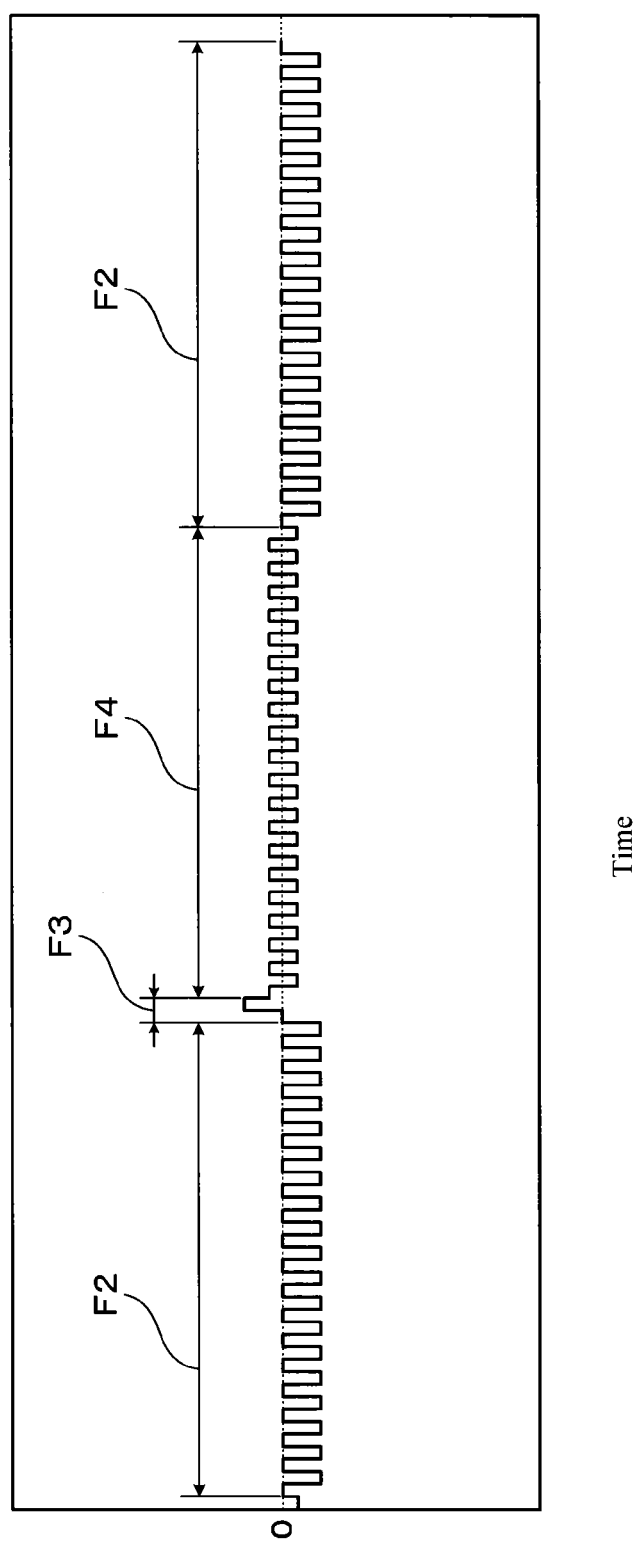
FIG. 9 is a diagram showing a waveform of an ion introduction current according to Example 1.

As shown in FIGS. 6 and 9, the ion introduction current is generated so as to allow successive repetition of: an ion introduction step S8 of causing a current of one polarity (F2 in FIG. 9) to flow to the contact part of the working electrode 11 and the skin; a reset pulse step S9 of causing a pulse current of the other polarity (F3 in FIG. 9) to flow to the contact part; and a skin care step S11 of causing a current whose polarities alternately change (F4 in FIG. 9) to flow to the contact part. Thereby, as the waveform of the ion introduction current flowing through the skin, the basic waveforms F2 to F4 shown in FIG. 9 are repeated.

Figure 7:
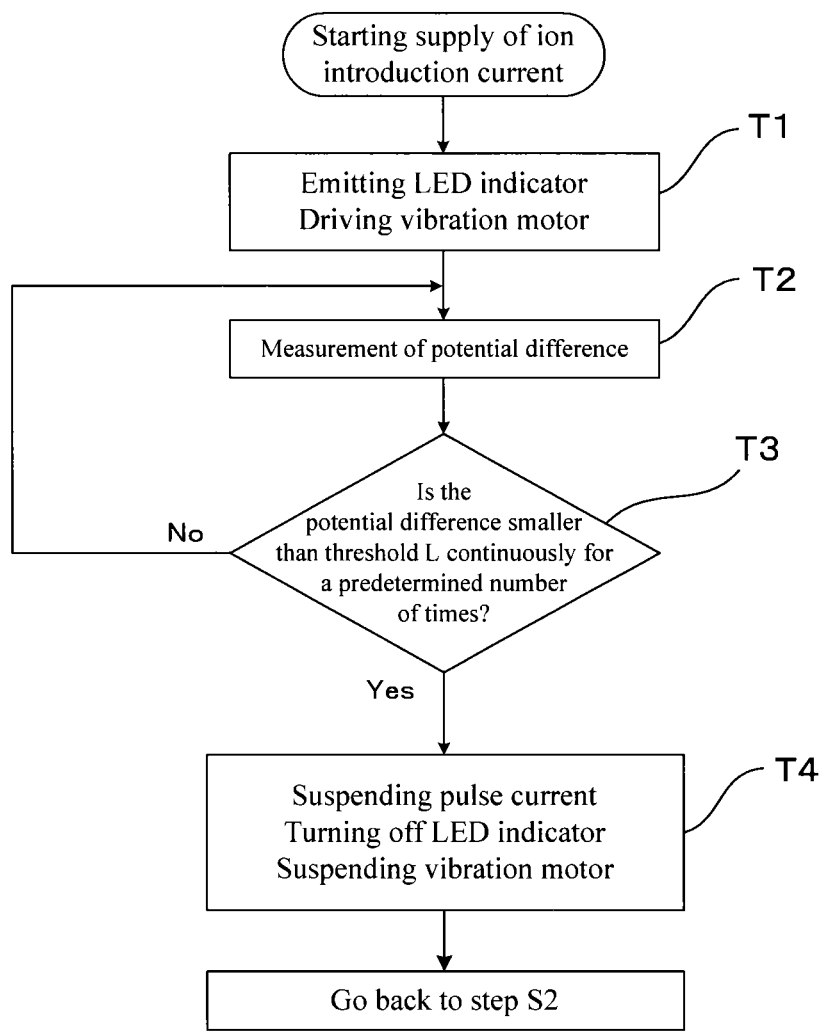
FIG. 7 is a flowchart illustrating the operation of a skin detection function while an ion introduction current flows, according to Example 1.

While the ion introduction current flows through the skin, the control microcomputer 30 causes the signal output section 302 to output drive signals to the LED indicator 13 and the vibration motor 14 (step T1 in FIG. 7). Thereby, the LED indicator 13 and the vibration motor 14 are driven while both the working electrode 11 and the counter electrode 12 are in contact with the human body.

More specifically, in the ion introduction step S8, the control microcomputer 30 applies the pulse voltage multiple times between the working electrode 11 and the counter electrode 12 while controlling the potential difference between these electrodes so that the potential of the working electrode 11 is lower than that of the counter electrode 12. Thereby, the working electrode 11 can cause the negative polarity pulse current to flow multiple times to the skin, as shown by the basic waveform F2 in FIG. 9.

In the reset pulse step S9, the control microcomputer 30 applies the pulse voltage once between the working electrode 11 and the counter electrode 12 while controlling the potential difference between these electrodes so that the potential of the working electrode is higher than that of the counter electrode 12. Thereby, the working electrode 11 can cause the positive polarity pulse current to flow to the skin, as shown by the basic waveform F3 in FIG. 9.

After the reset pulse step S9, the control microcomputer 30, as shown in FIG. 6, performs step S10 to output a current value selection signal to the constant current circuit 311 so as to set the current value to the skin care level.

As shown in FIG. 6, after performing step S10, the control microcomputer 30 performs the skin care step S11. In the skin care step S11, the control microcomputer applies, between the working electrode 11 and the counter electrode 12, a rectangular wave in which "high" and "low" of the potential difference of the working electrode 11 with respect to the counter electrode 12 alternately change. Thereby, the working electrode 11 can cause a current of a rectangular wave whose polarities alternately change between positive and negative, to flow to the skin, as shown by the basic waveform F4 in FIG. 9.

Further, as shown in FIG. 7, the control microcomputer 30 has a skin detection function of determining the contact state of the working electrode 11 and the counter electrode 12 with the human body, by using the pulse of the ion introduction current that flows through the human skin, in parallel to steps S7 to S11. In other words, by using the pulse currents flowing through the human skin in the ion introduction step S8, the reset pulse step S9, and the skin care step S11, the control microcomputer 30 is configured to perform measurement T2 of the potential difference in the reflux section 32 with respect to the ground potential, which potential difference is caused by the pulse currents, in a similar manner to step S5.

Then, as shown in FIG. 7, the control microcomputer 30 performs step T3 to determine the contact state of the working electrode 11 and the counter electrode with the human body, based on the result of the measurement of the potential difference in the reflux section 32. The determination in step T3 for the contact state of the working electrode 11 and the counter electrode 12 with the human body may be performed based on a result of measurement of a potential difference for a single pulse current, or based on total results of measurement of potential differences for a plurality of pulse currents. In addition, the pulse current(s) used for the determination of the contact state may be appropriately selected from among the pulse currents used in the ion introduction step S8, the reset pulse step S9, and the skin care step S11.

For example, in the present example, the determination of the contact state in step T3 is performed based on whether or not the potential difference between the both ends of the resistor 320, which is caused by the pulse current (F3 in FIG. 9) in the reset pulse step S9, goes below the threshold L continuously for a predetermined number of times. In other words, when the potential difference caused by the pulse current (F3 in FIG. 9) is smaller than the threshold L continuously for the predetermined number of times ("Yes" in step T3), the control microcomputer 30 of the present example determines that at least one of the working electrode 11 and the counter electrode 12 is not in contact with the human body. In this case, the control microcomputer 30 suspends generation of the ion introduction current, and suspends output of the drive signals to the LED indicator 13 and the vibration motor 14 (step T4). The control microcomputer 30 is configured to repeat steps S2 to S6 shown in FIG. 6 after step T4.

On the other hand, when the number of times the potential difference is continuously smaller than the threshold L does not reach the predetermined number of times ("No" in step T3), the control microcomputer 30 determines that both the working electrode 11 and the counter electrode 12 are in contact with the human body. While it is determined in step T3 that both the working electrode 11 and the counter electrode 12 are in contact with the human body, the control microcomputer 30 repeats steps S7 to S11 shown in FIG. 6.

Next, how to use the beauty tool 1 will be described. Before using the beauty tool 1, a user applies a cosmetic agent 4 containing a charged beautifying component to his/her skin. In the present example L-ascorbic acid-2-sodium phosphate is used as the beautifying component. As the cosmetic agent 4, a cosmetic agent which is composed to be attracted with a magnetic force and has a function of absorbing impurities or the like in the skin is used.

Figure 10:
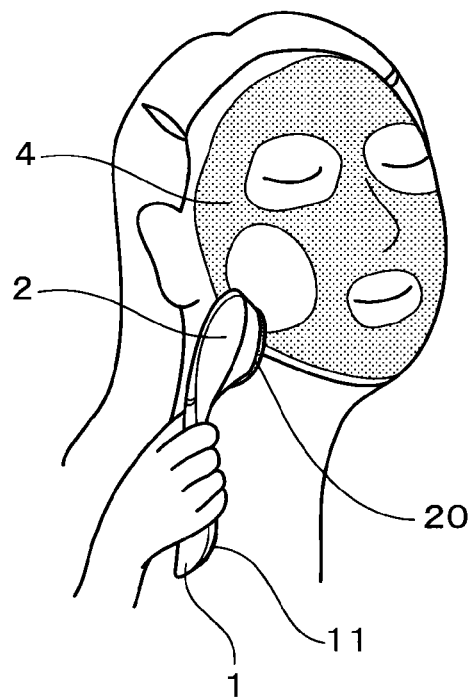
FIG. 10 is a diagram illustrating how to use the beauty tool to remove a cosmetic agent, according to Example 1.

After application of the cosmetic agent 4, the user holds the main body 10 at the working electrode 11 side, and brings the magnetic force generating surface 20 side of the attraction head 2 close to the skin as shown in FIG. 10. At this time, a detachable cover member may be attached to the magnetic force generating surface 20 in advance. The shape, material, and the like of the cover member are not limited as long as the cover member can cover the magnetic force generating surface 20, and various types of cover members may be used. In the present example, sheet-formed cotton is wound around the attraction head 2 (not shown).

Thereby, as described above, the used cosmetic agent 4 that has absorbed impurities and the like in the skin is removed from the surface of the skin, and attracted onto the attraction head 2. At this time, L-ascorbic acid-2-sodium phosphate as the beautifying component in the cosmetic agent 4 is not attracted by the magnetic force but remains on the surface of the skin. The used cosmetic agent 4 attracted onto the attraction head 2 can be removed from the magnetic force generating surface 20 together with the cover member, and discarded.

Figure 11:
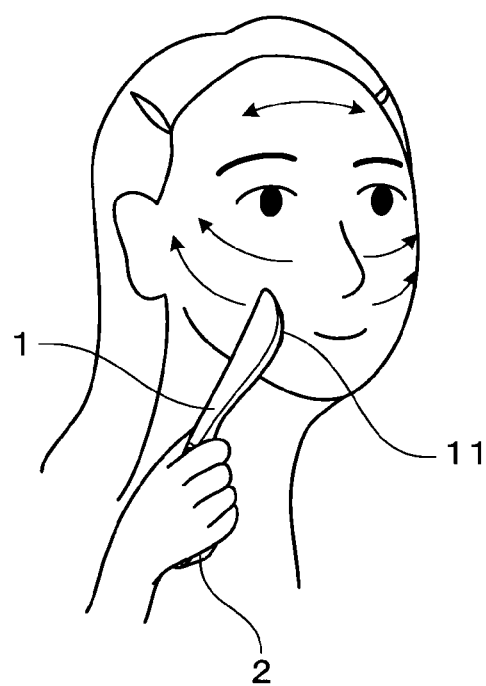
FIG. 11 is a diagram illustrating how to use the beauty tool to allow a beautifying component to infiltrate into skin, according to Example 1.

After removal of the used cosmetic agent 4 from the skin, the user changes the manner of holding the main body 10 so that the working electrode 11 projects from the hand and the counter electrode 12 is in contact with the hand. Then, as shown in FIG. 11, the user brings the working electrode 11 into contact with the skin surface. Thereby, the ion introduction current composed of repetition of the basic waveforms F2 to F4 shown in FIG. 9 flows through the contact part of the working electrode 11 and the skin. In the present example, in the ion introduction step S8, the working electrode 11 and the counter electrode 12 act as a negative electrode and a positive electrode, respectively, and a negative polarity current flows to the skin surface in contact with the working electrode 11. Thus, the beauty tool 1 can allow L-ascorbic acid-2-phosphate anion as an anion to infiltrate into the skin.

Next, the function and effect of the beauty tool will be described. The beauty tool 1 includes the attraction head 2 for attracting and removing the cosmetic agent 4 by means of a magnetic force. Therefore, as shown in FIG. 10, when the user holds the main body 10 and brings the attraction head 2 close to the skin surface on which the cosmetic agent 4 is applied, the cosmetic agent 4 is attracted to the attraction head 2 due to the magnetic force. As a result, the beauty tool 1 can easily remove the used cosmetic agent 4.

As shown in FIG. 2, the beauty tool 1 includes the working electrode 11 for causing the ion introduction current to flow to the contact part when being in contact with the human skin. Therefore, when the user, who has previously applied the charged beautifying component to the skin, brings the working electrode 11 into contact with the skin so that the ion introduction current flows to the skin, the beautifying component is more likely to migrate toward the inside of the skin. As a result, the beauty tool 1 promotes infiltration of the beautifying component, and allows the beautifying component to rapidly exert the beauty effect.

The beauty tool 1 includes both the attraction head 2 and the working electrode 11. Therefore, as described above, the beauty tool 1 can realize both the process of removing impurities and waste from the skin with the cosmetic agent 4 and the process of allowing the charged beautifying component to infiltrate into the skin due to the ion introduction current, by using one tool. As a result, the user need not prepare and use different tools for the two processes.

Further, as shown in FIG. 4, the permanent magnet 200 is provided in the attraction head 2. Therefore, the attraction head 2 can easily and stably generate a relatively strong magnetic force. As a result, the beauty tool 1 can easily remove the used cosmetic agent 4 from the skin. Since the permanent magnet 200 is adopted, power for generating a magnetic force is dispensed with.

As shown in FIG. 1, the attraction head 2 includes the magnetic force generating surface 20 facing in a direction (lower direction) substantially perpendicular to the longitudinal direction of the main body 10. Therefore, as shown in FIG. 10, when holding the main body 10, the user can easily turn the magnetic force generating surface 20 to the skin surface on which the cosmetic agent 4 is applied. As a result, the beauty tool 1 becomes more convenient for the user.

The main body 10 includes, as shown in FIG. 2, the counter electrode 12 on the side (upper side) opposite to the magnetic force generating surface 20, and includes, as shown in FIG. 3, the working electrode 11 disposed facing the lower side. Therefore, as described above, when the beauty tool 1 is placed on a desk or the like, the possibility of conduction between the working electrode 11 and the counter electrode 12 via the surface on which the beauty tool 1 is placed is reduced, and thus power consumption of the beauty tool 1 can be easily reduced. In addition, since the closed current path is formed passing through the power supply 33 and the human body, the beauty tool 1 can cause the ion introduction current to flow to the human body more efficiently. As a result, the beauty tool 1 can further enhance the beauty effect.

Figure 5:
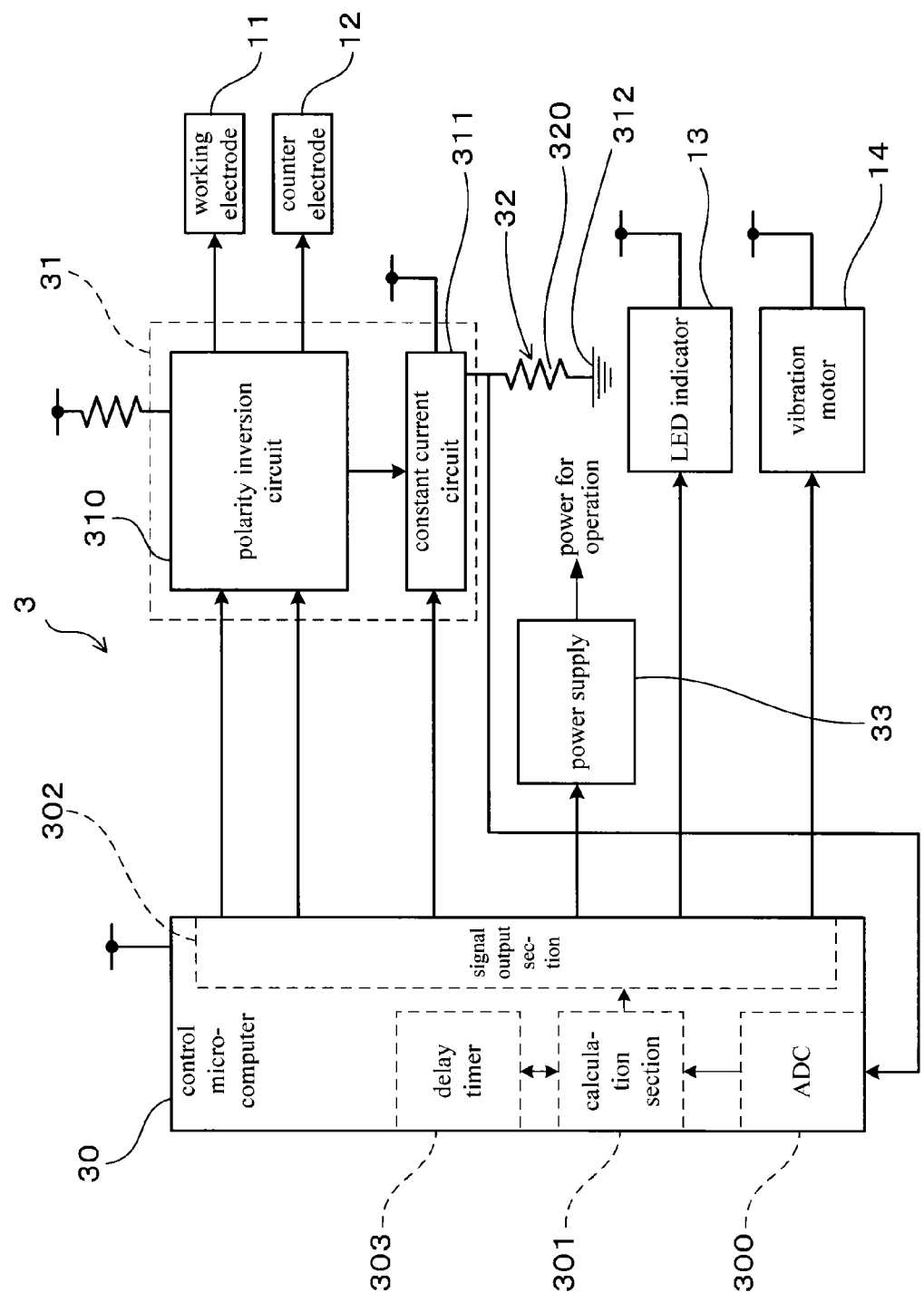
FIG. 5 is a block diagram illustrating a configuration of a controller of the beauty tool according to Example 1.

As shown in FIGS. 5 and 6, the controller 3 includes: the means to apply a pulse voltage to the working electrode 11 and measure an electrical characteristic value in the controller 3 by using the pulse voltage; the means to determine whether or not the working electrode 11 and the counter electrode 12 are in contact with the human body, based on the electrical characteristic value; and the means to cause the ion introduction current to flow to the contact part when it is determined that both the working electrode 11 and the counter electrode 12 are in contact with the human body. The controller 3 is configured to perform the measurement of the electrical characteristic value and the determination again after waiting for a lapse of a predetermined time by using the delay timer 303 when it is determined that at least one of the working electrode 11 and the counter electrode 12 is not in contact with the human body.

Therefore, the beauty tool 1 can cause the ion introduction current to flow to the contact part when both the working electrode 11 and the counter electrode 12 come into contact with the human body, without the necessity of an additional switching operation. Thereby, the user can easily obtain the effect of promoting infiltration of the beautifying component by only holding the main body 10 at the counter electrode 12 side so that the hand contacts the counter electrode 12, and bringing the working electrode 11 into contact with a portion where the user desires the beauty effect.

The beauty tool 1 can reduce the frequency of performing the measurement of the electrical characteristic value and the determination, by causing the delay timer 303 to operate as described above. As a result, the beauty tool 1 can reduce power consumption in the standby state, namely, the state where at least one of the working electrode 11 and the counter electrode 12 is not in contact with the human body.

As shown in FIGS. 5 and 6, the controller 3 includes the reflux section 32 which takes in the current flowing through the human body and refluxes the current to the power supply 33, and is configured to measure, as an electrical characteristic value, a potential difference of the reflux section 32 with respect to the ground potential, and determine that both the working electrode 11 and the counter electrode 12 are in contact with the human body when the potential difference is equal to or larger than a predetermined threshold. Therefore, the circuit configuration of the controller 3 can be easily simplified as described above, and the accuracy of the determination as to whether the working electrode 11 and the counter electrode 12 are in contact with the human body can be increased.

As shown in FIGS. 6 and 9, the ion introduction current is generated so as to allow successive repetition of: the ion introduction step S8 of causing a current of one polarity (F2 in FIG. 9) to flow to the contact part; the reset pulse step S9 of causing a pulse current of the other polarity (F3 in FIG. 9) to flow to the contact part; and the skin care step S11 of causing a current whose polarities alternately change (F4 in FIG. 9) to flow to the contact part. Therefore, as described above, the beauty tool 1 is expected to further enhance the beauty effect by synergy of the effect of promoting infiltration of the beautifying component into the skin and the effect of activating the skin.

Further, the beauty tool 1 includes the vibration motor 14 at an end portion on the working electrode 11 side, and is configured so that the vibration motor 14 is driven while the ion introduction current flows through the human skin. Therefore, vibration generated from the vibration motor 14 may provide advantageous effects, such as smooth flow of lymph, promoted circulation of blood, enhanced metabolism, and the like, in the contact part of the working electrode 11 and the skin and its vicinity. As a result, the beauty tool 1 can further enhance the beauty effect that the user can feel.

Furthermore, in the present example, a cosmetic agent containing a beautifying component that has been charged in advance is used as the cosmetic agent 4 used in combination with the beauty tool 1. Therefore, the user can apply the beautifying component to the skin simultaneously with application of the cosmetic agent 4 to the skin. As a result, the user can perform, more efficiently, removal of impurities and the like from the skin, and promotion of infiltration of the beautifying component into the skin.

As described above, the beauty tool 1 can improve the convenience in successively performing the process of removing impurities and waste from the skin, and the process of allowing the beautifying component to infiltrate into the skin.

Example 2

Figure 12:
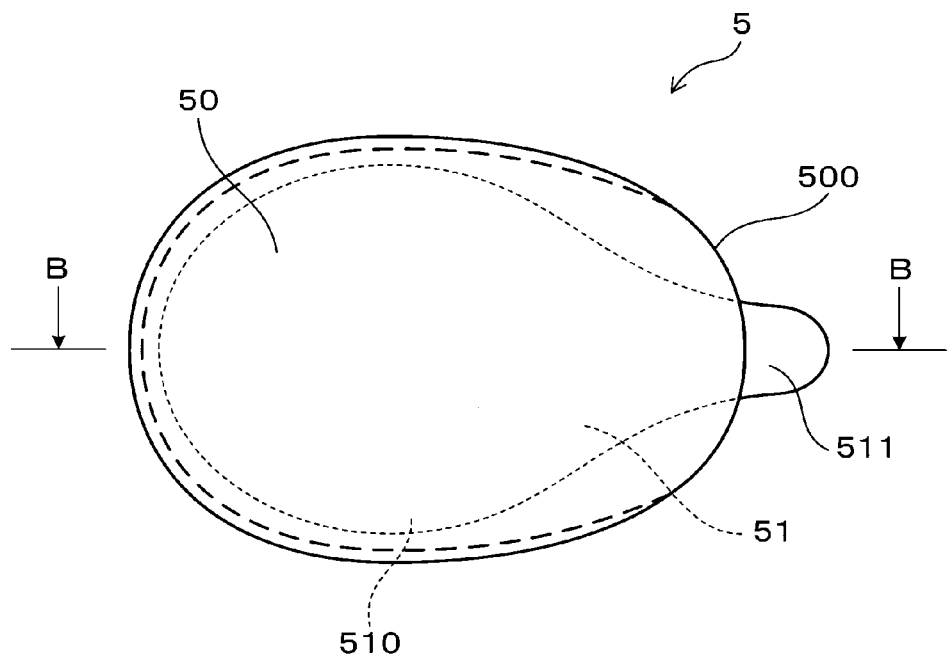
FIG. 12 is a plan view of a cover member according to Example 2.
Figure 15:
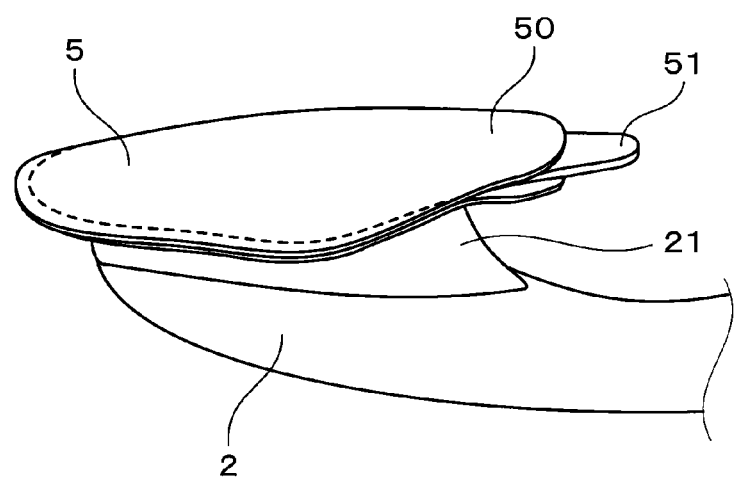
FIG. 15 is a plan view showing a state where the cover member is attached to the beauty tool, according to Example 2.

This example relates to a cover member 5 which is attachable to the beauty tool 1 according to Example 1. As shown in FIGS. 12 and 15, the cover member 5 according to the present example includes a cover body 50 that covers the magnetic force generating surface 20 of the beauty tool 1, and a magnet sheet 51 as a retaining means for retaining the cover body 50 on the magnetic force generating surface 20.

Figure 13:
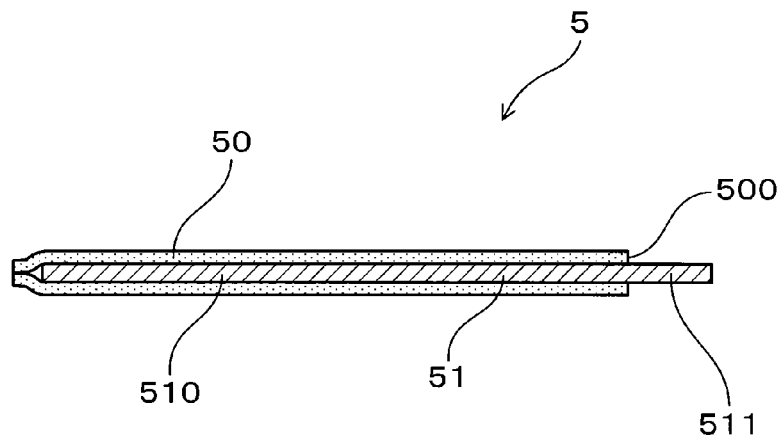
FIG. 13 is a cross-sectional view as viewed from the direction of arrows B-B in FIG. 12.
Figure 14:
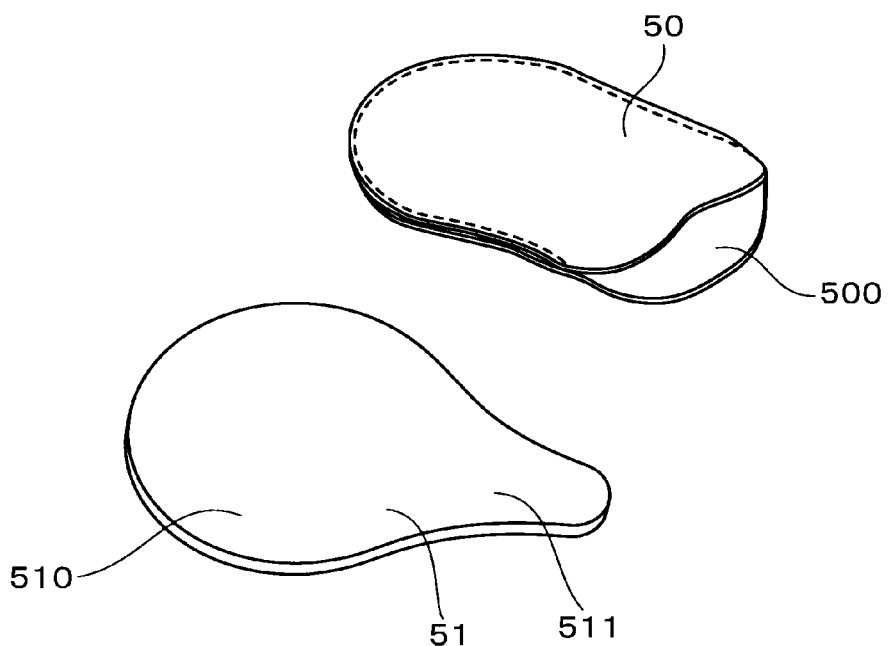
FIG. 14 is a perspective view showing a state where a magnet sheet of the cover member is detached from a cover body, according to Example 2.

As shown in FIGS. 13 and 14, the cover body 50 has a double-layer structure obtained by putting two cotton sheets together and joining peripheral edges thereof with an insertion opening 500 being left open. The cover body 50 is composed of two cotton sheets. Each cotton sheet is formed in a substantially elliptical shape and has a size larger than that of the magnetic force generating surface 20. As shown in FIG. 12, the outer peripheral edges of the two cotton sheets are joined to each other so that portions thereof at one end in the longitudinal direction are not joined. The unjoined portions of the outer peripheral edges form the insertion opening 500.

As shown in FIG. 13, the cover body 50 is configured so that the magnet sheet 51 can be inserted from the insertion opening 500 and placed in a housing space formed between the two cotton sheets. The two cotton sheets may be joined by known methods such as stitching, bonding, and the like.

As shown in FIG. 14, the magnet sheet 51 inserted and placed in the cover body 50 has an attraction portion 510 of a substantially elliptical shape, and a holding portion 511 formed to project from one end of the attraction portion 510 in the longitudinal direction. In addition, the magnet sheet 51 can be obtained by, for example, dispersing powdery permanent magnet in a flexible resin, and forming the resin into a sheet shape. The magnet sheet 51 of the present example is configured to be insertable from the insertion opening 500 of the cover body 50, with the attraction portion 510 being bent.

As shown in FIGS. 12 and 13, the holding portion 511 is formed to be exposed to the outside of the cover body 50 from the insertion opening 500 in the state where a front end of the attraction portion 510 is inserted deep into the cover body 50.

By using the cover member 5 configured as described above, after the cover member 5 is detached from the magnetic force generating surface 20, the used cosmetic agent 4 is retained on the surface of the cover body 50 due to the magnetic force generated from the magnet sheet 51. As a result, the used cosmetic agent 4 is prevented from unintentionally falling from the cover member 5 and spattering.

As shown in FIGS. 12 and 13, the cover body 50 has the double-layer structure obtained by putting two layers together and joining the peripheral edges thereof so that the insertion opening 500 is formed, and allows the magnet sheet 51 to be inserted from the insertion opening 500 and placed in the housing space formed between the two layers. Therefore, the magnet sheet 51 is attachable to and detachable from the cover body 50, and thus only the cover body 50 can be replaced. As a result, as described above, disposal of the used cosmetic agent 4 is facilitated. Further, the cover body 50 can be easily kept clean.

The cover body 50 is formed of the cotton sheets. Therefore, even if the cotton sheets come in contact with the skin, stimulus to the skin may be easily reduced. Thus, the user can conform the beautifying component to the skin or remove the excessive beautifying component by using the cotton sheet contacting the skin. As a result, the beauty effect can be further enhanced.

Example 3

Figure 16:
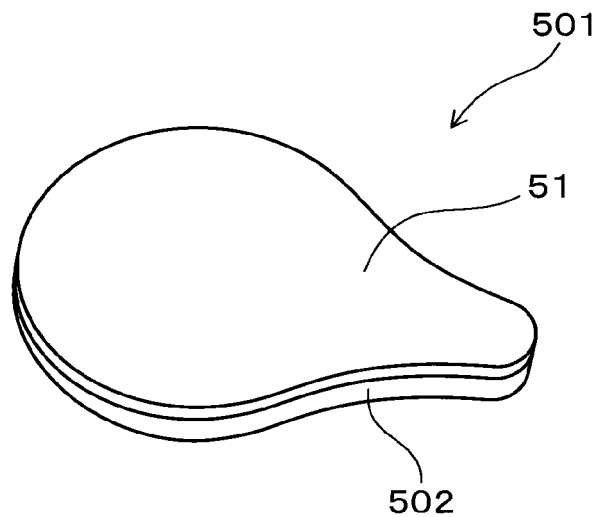
FIG. 16 is a perspective view of a cover member joined to a magnet sheet, according to Example 3.

In this example, the cover body 50 and the magnet sheet 51 of the cover member 5 according to Example 2 are integrated with each other. As shown in FIG. 16, a cover member 501 of the present example is obtained by bonding, to one main surface of the magnet sheet 51 of Example 2, a cover body 502 formed in the same shape as the magnet sheet 51. The cover body 502 is formed of a cotton sheet. In other respects, the present example is identical to Example 2.

Thus, even when the cover body 502 and the magnet sheet 51 are integrally bonded, the same function and effect as those of Example 2 can be achieved.

Example 4

Figure 17:
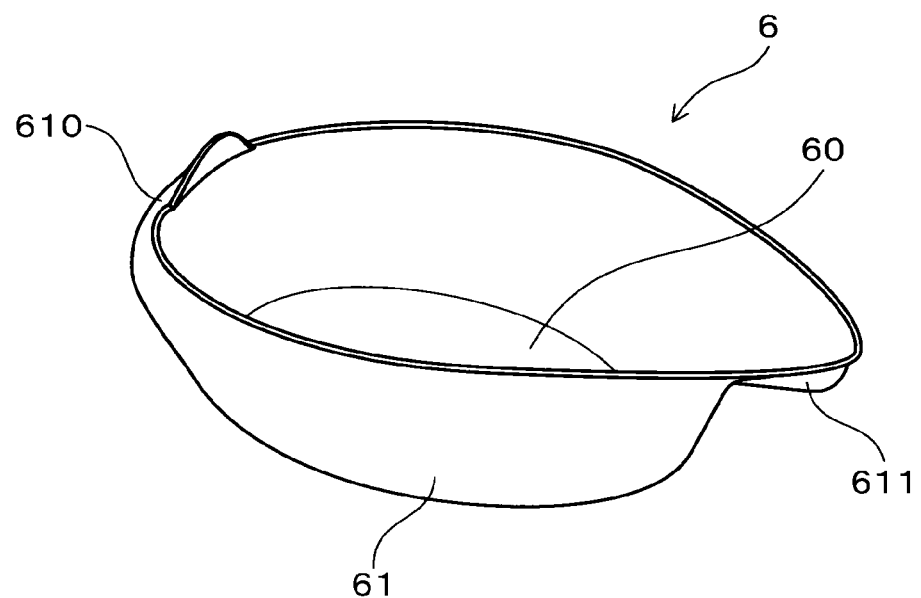
FIG. 17 is a perspective view of a cover member configured to be inside-outside reversely transformable according to Example 4.
Figure 21:
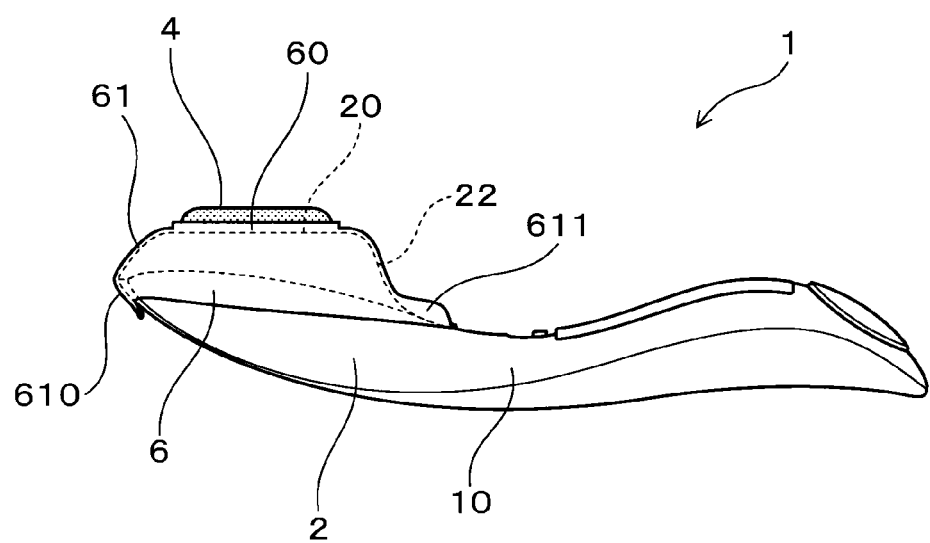
FIG. 21 is a plan view showing a state where a cosmetic agent is attracted to the beauty tool, according to Example 4.
Figure 22:
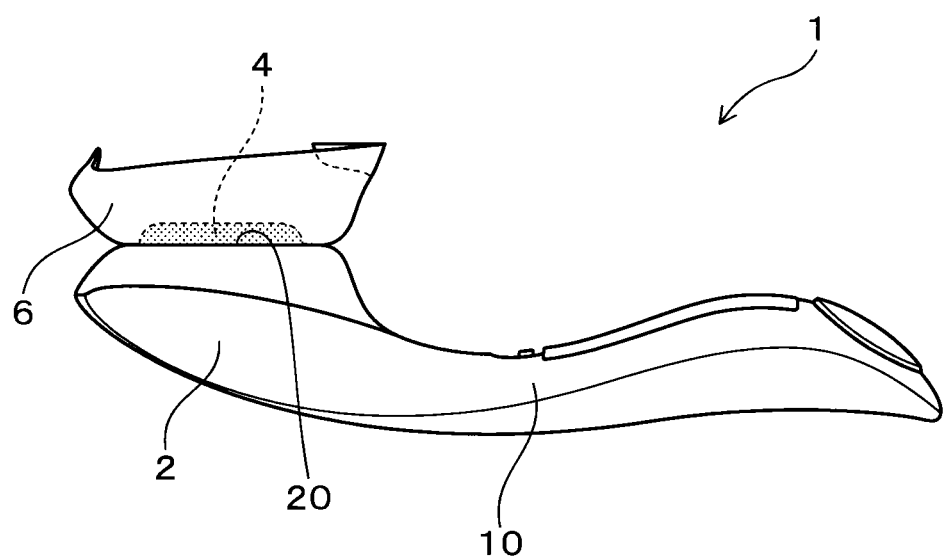
FIG. 22 is a plan view showing a state where the cover member is reversed inside out, according to Example 4.

In this example, a cover member attachable to the beauty tool 1 of Example 1 is formed in a substantially cup-like shape. As shown in FIGS. 17 and 21, a cover member 6 of the present example has a bottom surface portion 60 facing the magnetic force generating surface 20, and has a substantially cup-like shape similar to the shape of the swelling portion 21. As shown in FIGS. 21 and 22, the cover member 6 is configured to be inside-outside reversely transformable such that the projecting direction of the bottom surface portion 60 is reversible.

Figure 18:
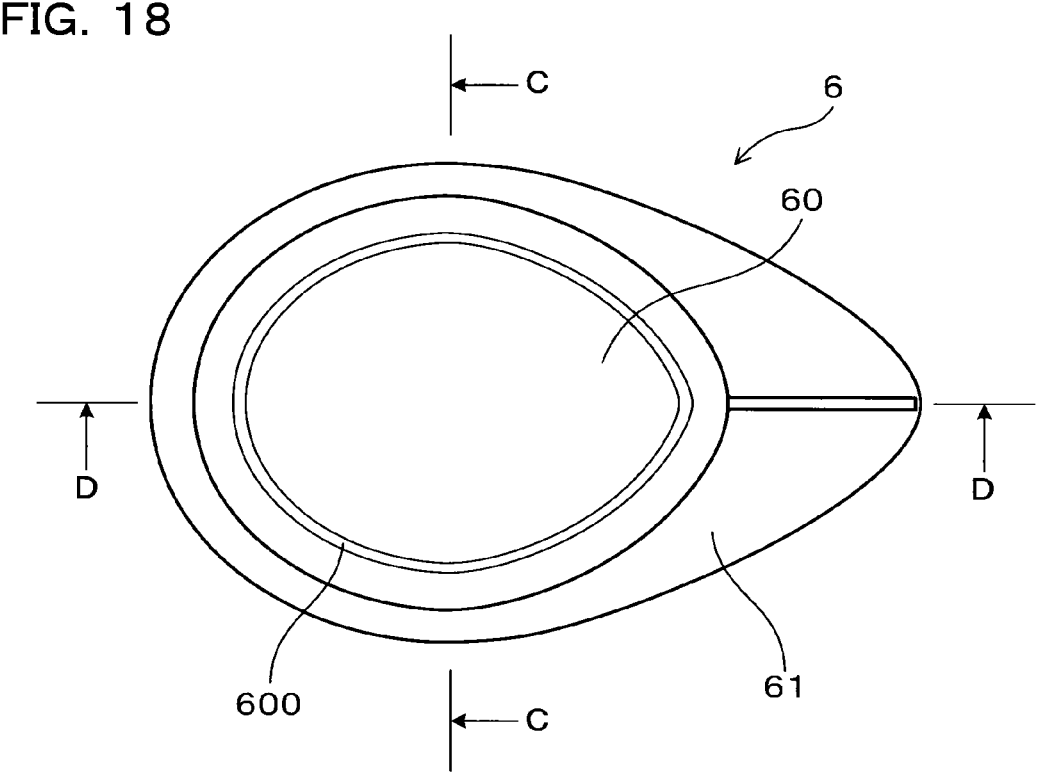
FIG. 18 is a plan view of the cover member according to Example 4, as viewed from the lower side.

The cover member 6 is formed of a silicone rubber having elasticity. As shown in FIG. 17, the cover member 6 has the flat bottom surface portion 60, and a sidewall portion 61 extending from the outer peripheral edge of the bottom surface portion 60 so as to have a gradually increasing diameter. As shown in FIG. 18, the bottom surface portion 60 has a substantially elliptical shape as viewed in its thickness direction. Thereby, the cover member 6 has a substantially cup-like shape. In addition, as shown in FIG. 21, the cover member 6 is disposed such that, when being attached to the swelling portion 21 of the beauty tool 1, the bottom surface portion 60 fits to the magnetic force generating surface 20 and the sidewall portion 61 fits to the head sidewall 22.

Figure 19:
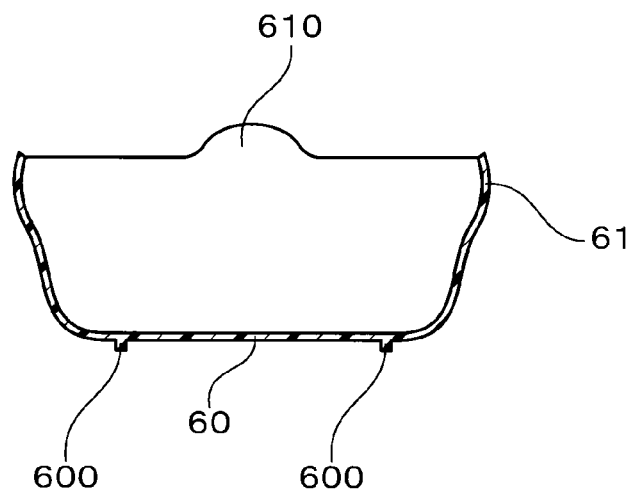
FIG. 19 is a cross-sectional view as viewed from the direction of arrows C-C in FIG. 18.
Figure 20:
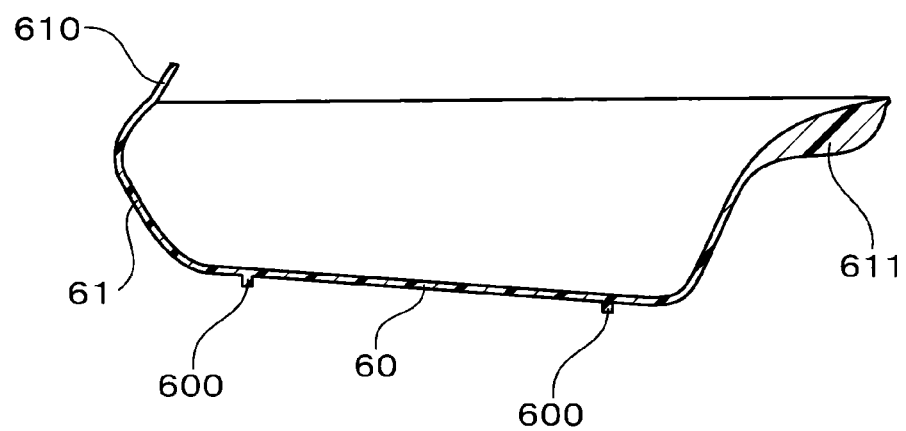
FIG. 20 is a cross-sectional view as viewed from the direction of arrows D-D in FIG. 18.

As shown in FIGS. 18 to 20, the bottom surface portion 60 has a projecting ring portion 600 that projects in the thickness direction at the outer peripheral edge thereof, and annularly surrounds the entirety of the outer peripheral edge. In the state where the cover member 6 is attached to the swelling portion 21, the projecting ring portion 600 is disposed on a surface of the bottom surface portion 60 opposite to the magnetic force generating surface 20.

As shown in FIGS. 17 and 20, the sidewall portion 61 has an engagement portion 610 at one end of the bottom surface portion 60 in the longitudinal direction, and an extending ear-like portion 611 at the other end thereof. The engagement portion 610 and the extending ear-like portion 611 have a function of fixing the cover member 6 to the swelling portion 21.

The engagement portion 610 is formed by extending the sidewall portion 61 of the cover member 6. In the state where the cover member 6 is attached to the attraction head 2, the engagement portion 610, as shown in FIG. 21, has a shape fitting to the outer surface of the attraction head 2, and is disposed so as to cover a rear end portion of the attraction head 2. Thereby, the cover member 6 is configured to be engageable with the attraction head 2 such that the rear end portion of the attraction head 2 is housed in the engagement portion 610.

The extending ear-like portion 611 is provided at an edge of the sidewall portion 61 on the opposite side from the engagement portion 610. As shown in FIGS. 17 and 21, the extending ear-like portion 611 is formed so as to extend from the edge of the sidewall portion 61 frontward (toward the working electrode 11) along the main body 10 of the beauty tool 1. Thereby, the cover member 6 is configured such that, when the user removes the cosmetic agent 4, the user can hold the extending ear-like portion 611 together with the main body 10. The cover member 6 is configured to maintain the state of being attached to the attraction head 2 by the user's holding the extending ear-like portion 611 together with the main body 10.

Next, the function and effect of the cover member 6 of the present example will be described. As described above, the cover member 6 has a substantially cup-like shape, and is configured to be inside-outside reversely transformable. Therefore, as shown in FIGS. 21 and 22, by transforming the cover member 6 so as to be reversed inside out, the used cosmetic agent 4 attracted to the magnetic force generating surface 20 can be stored in the cover member 6. As a result, when the user pulls off the cover member 6 from the attraction head 2, the cosmetic agent 4 is prevented from unintentionally spattering.

Further, the user can easily remove the used cosmetic agent 4 from the surface of the cover member 6 by bringing the cover member 6 above a place where the cosmetic agent 4 is to be discarded, and turning the surface with the cosmetic agent 4 downward to urge natural falling of the cosmetic agent 4 due to its own weight or performing a process of removing the cosmetic agent 4 with paper or the like. The cover member 6 from which the cosmetic agent 4 has been removed is again transformed to be reversed inside out and attached to the attraction head 2 of the beauty tool 1, and thus the cover member 6 can be used again.

The cover member 6 is formed of a silicone rubber having elasticity. Therefore, the cover member 6 can be easily transformed to be reversed inside out. Moreover, it is very easy to restore the cover member 6 to its initial shape.

As shown in FIG. 17, the cover member 6 has the flat bottom surface portion 60, and the sidewall portion 61 extending from the outer peripheral edge of the bottom surface portion 60 so as to have a gradually increasing diameter. Therefore, the cover member 6 can be transformed to be reversed inside out by displacing only the sidewall portion 61 with the position of the bottom surface portion 60 being kept. As a result, the process of transforming the cover member 6 to be reversed inside out is facilitated, and thus spattering of the cosmetic agent 4 from the cover member 6 can be prevented more reliably.

As shown in FIG. 18, the cover member 6 of the present example includes, at the outer peripheral edge of the bottom surface portion 60, the projecting ring portion 600 that projects in the thickness direction and annularly surrounds the entirety of the outer peripheral edge. Therefore, the used cosmetic agent 4 can be easily retained on the inner circumferential side of the bottom surface portion 60 relative to the projecting ring portion 600, and thereby the amount of the cosmetic agent 4 attracted to the outer circumferential side relative to the projecting ring portion 600 can be easily reduced. As a result, the user can easily hold the outer circumferential side relative to the projecting ring portion 600, which allows the user to perform the inside-outside reverse transformation of the cover member 6 more easily.

The cover member 6 of the present example has the engagement portion 610 and the extending ear-like portion 611. Therefore, the cover member 6 is configured to maintain the state of being attached to the attraction head 2 as described above by action of at least one of the engagement portion 610 and the extending ear-like portion 611.

Example 5

In this example, the substantially cup-like shaped cover member 6 according to Example 4 is formed of a material that is not inside-outside reversely transformable. The cover member (not shown) of the present example is formed of 0.3 mm thick polyethylene so as to have the same shape as the cover member 6 of Example 4. The material of the cover member of the present example is not limited to polyethylene, and various plastic materials may be used. The cover member can be produced by molding the plastic material by a known molding method represented by vacuum molding or the like.

The cover member 6 of the present example can be produced with high productivity at low cost. In addition, as in Example 1, the cover member 6 allows removal of the used cosmetic agent 4 from the skin surface without soiling the attraction head 2.

In Examples 1 to 5, the working electrode 11 and the counter electrode 12 are caused to act as a negative electrode and a positive electrode, respectively, in the ion introduction step S8. However, the negative electrode and the positive electrode may be interchanged according to the composition of the beautifying component. For example, when the beautifying component to be introduced into the skin is a cation, the potential of the working electrode 11 is set to be higher than that of the counter electrode 12 in the ion introduction step S8.

In the Examples 1 to 5, the predetermined time set on the delay timer 303 is 200 msec. However, the predetermined time may be appropriately set within a range from 50 msec to 1000 msec. When the predetermined time is shorter than 50 msec, the frequency of performing the measurement of the electrical characteristic value (step S5) and the determination of the contact state (step S6) is relatively high. Thereby, power consumption in steps S2 to S6 is likely to be increased. On the other hand, when the predetermined time exceeds 1000 msec, the frequency of performing the measurement and the determination is excessively low, and thereby a time lag from when the working electrode 11 comes in contact with the human body to when the measurement and the determination are performed might be increased. The increased time lag might degrade the convenience of the beauty tool. Therefore, from the viewpoint of both low power consumption and convenience, the predetermined time is preferably not shorter than 50 msec but not longer than 1000 msec.

The shape of the cover member is not limited to the shapes described in Examples 1 to 5. Various shapes may be adopted for the cover member as long as the cover member can cover the magnetic force generating surface 20.

In Examples 1 to 5, the beauty tool 1 is configured so that a magnetic force is constantly generated from the magnetic force generating surface 20. However, the beauty tool 1 may be provided with a magnetic force control means for switching between a state where a magnetic force is generated from the magnetic force generating surface 20 and a state where a magnetic force is not generated from the magnetic force generating surface 20. In this case, a magnetic force can be generated from the magnetic force generating surface 20 only when attraction and removal of the cosmetic agent 4 applied to the skin are performed, and thereby the magnetic force from the magnetic force generating surface 20 is prevented from unintentionally acting on the surroundings of the beauty tool 1. Further, by switching the beauty tool 1 to the state where no magnetic force is generated, the cosmetic agent 4 attracted to the magnetic force generating surface can be easily removed from the beauty tool 1 and discarded after the cosmetic agent 4 has been attracted and removed from the skin. Thus, the beauty tool 1 having the magnetic force control means becomes more convenient.

The magnetic force generating means can be realized by, for example, a configuration in which a magnet (the permanent magnet 200 or an electromagnet) embedded in the attraction head 2 is rotated or slid so as to be separated from the magnetic force generating surface 20, or a configuration in which a movable yoke member is inserted between the magnet and the magnetic force generating surface 20 to shield the magnetic flux. When an electromagnet is used, a switch for switching the electromagnet between its ON state and its OFF state may be provided, and thus the switch can be caused to act as a magnetic force generating means.

What is claimed is:

1. A beauty tool, comprising:
   a substantially rod-shaped main body;
   an attraction head provided at one elongate end of the main body, and including a magnetic force generating surface to attract and remove a cosmetic agent applied to human skin using magnetic force, a permanent magnet embedded within the attraction head; and
   a beauty effect imparting part provided at the other elongate end of the main body, to impart a beauty effect to the human skin in a state where the beauty effect imparting part is in contact with or close to the human skin, the beauty effect imparting part including a working electrode.

2. The beauty tool according to claim 1, wherein the attraction head includes the magnetic force generating surface facing in a direction substantially perpendicular to a longitudinal direction of the main body.

3. The beauty tool according to claim 1, wherein
   the beauty effect imparting part comprises a working electrode that causes an ion introduction current to flow to a contact part when in contact with the human skin, and
   the main body includes a power supply to supply power to the working electrode and a controller to control the current flowing to the contact part.

4. The beauty tool according to claim 3, wherein
   the main body comprises, a counter electrode on a side opposed to the magnetic force generating surface, the counter electrode is configured to be able to form a closed current path passing through the power supply and a human body together with the working electrode, and
   the working electrode is disposed so as to face a side the magnetic force generating surface faces.

5. The beauty tool according to claim 3, wherein
   the controller includes circuitry configured to:
   apply a pulse voltage to the working electrode, and measure an electrical characteristic value in the controller;
   determine whether or not the working electrode is in contact with the human body, based on the electrical characteristic value; and
   cause the ion introduction current to flow to the contact part when it is determined that the working electrode is in contact with the human body, and
   the controller is configured to, when it is determined that the working electrode is not in contact with the human body, perform a measurement of the electrical characteristic value and the determination again after waiting for a lapse of a predetermined time by using a delay timer.

6. The beauty tool according to claim 5, wherein the controller:
   includes a reflux section that takes in the current flowing through the human body, and refluxes the current to the power supply,
   measures a potential difference of the reflux section with respect to a ground potential, as the electrical characteristic value, and
   determines that the working electrode is in contact with the human body when the potential difference is equal to or larger than a predetermined threshold.

7. The beauty tool according to claim 3, wherein the ion introduction current allows the following to be successively repeated: causing a current of a first polarity to flow to the contact part; causing a pulse current of a second polarity to flow to the contact part; and causing a current whose polarities alternately change to flow to the contact part.

8. A beauty tool, comprising:
   a substantially rod-shaped main body;
   an attraction head provided at one elongate end of the main body, and including a magnetic force generating surface to attract and remove a cosmetic agent applied to human skin using magnetic force, an electromagnet embedded within the attraction head; and
   a beauty effect imparting part provided at the other elongate end of the main body, to impart a beauty effect to the human skin in a state where the beauty effect imparting part is in contact with or close to the human skin, the beauty effect imparting part including a working electrode.

9. The beauty tool according to claim 8, wherein the attraction head includes the magnetic force generating surface facing in a direction substantially perpendicular to a longitudinal direction of the main body.

10. The beauty tool according to claim 8, wherein the beauty effect imparting part comprises a working electrode that causes an ion introduction current to flow to a contact part when in contact with the human skin, and
    the main body includes a power supply to supply power to the working electrode and a controller to control the current flowing to the contact part.

11. The beauty tool according to claim 10, wherein
    the main body comprises, a counter electrode on a side opposed to the magnetic force generating surface, the counter electrode is configured to be able to form a closed current path passing through the power supply and a human body together with the working electrode, and the working electrode is disposed so as to face a side the magnetic force generating surface faces.

12. The beauty tool according to claim 10, wherein the controller includes circuitry configured to:

apply a pulse voltage to the working electrode, and measure an electrical characteristic value in the controller;

determine whether or not the working electrode is in contact with the human body, based on the electrical characteristic value; and cause the ion introduction current to flow to the contact part when it is determined that the working electrode is in contact with the human body, and the controller is configured to, when it is determined that the working electrode is not in contact with the human body, perform a measurement of the electrical characteristic value and the determination again after waiting for a lapse of a predetermined time by using a delay timer.

13. The beauty tool according to claim 12, wherein the controller:

includes a reflux section that takes in the current flowing through the human body, and refluxes the current to the power supply, measures a potential difference of the reflux section with respect to a ground potential, as the electrical characteristic value, and determines that the working electrode is in contact with the human body when the potential difference is equal to or larger than a predetermined threshold.

14. The beauty tool according to claim 10, wherein the ion introduction current allows the following to be successively repeated: causing a current of a first polarity to flow to the contact part; causing a pulse current of a second polarity to flow to the contact part; and causing a current whose polarities alternately change to flow to the contact part.

* * * * *